US008268588B2

(12) United States Patent
Egrie et al.

(10) Patent No.: US 8,268,588 B2
(45) Date of Patent: Sep. 18, 2012

(54) METHODS AND COMPOSITIONS FOR THE PREVENTION AND TREATMENT OF ANEMIA

(75) Inventors: Joan C. Egrie, Newbury Park, CA (US); Steven G. Elliott, Newbury Park, CA (US); Jeffrey K. Browne, Camarillo, CA (US); Karen C. Sitney, Studio City, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/168,913

(22) Filed: Jun. 24, 2011

(65) Prior Publication Data
US 2011/0256586 A1 Oct. 20, 2011

Related U.S. Application Data

(60) Division of application No. 11/977,845, filed on Oct. 26, 2007, now Pat. No. 7,973,009, which is a division of application No. 09/723,955, filed on Nov. 27, 2000, now Pat. No. 7,304,150, which is a continuation of application No. 09/559,001, filed on Apr. 21, 2000, now abandoned, which is a continuation-in-part of application No. 09/178,292, filed on Oct. 23, 1998, now abandoned.

(51) Int. Cl.
C12N 15/00 (2006.01)
C12N 5/00 (2006.01)
C12N 1/00 (2006.01)
C07K 14/505 (2006.01)

(52) U.S. Cl. .................... 435/69.1; 435/325; 435/320.1; 530/397

(58) Field of Classification Search .................. None
See application file for complete search history.

(56) References Cited

U.S. PATENT DOCUMENTS

| 4,397,840 | A | 8/1983 | Takezawa et al. |
| 4,419,446 | A | 12/1983 | Howley et al. |
| 4,667,016 | A | 5/1987 | Lai et al. |
| 4,703,008 | A | 10/1987 | Lin |
| 4,806,524 | A | 2/1989 | Kawaguchi et al. |
| 5,041,376 | A | 8/1991 | Gething et al. |
| 5,217,881 | A | 6/1993 | Park |
| 5,218,092 | A | 6/1993 | Sasaki et al. |
| 5,378,808 | A | 1/1995 | D'Andrea et al. |
| 5,416,071 | A | 5/1995 | Igari et al. |
| 5,480,981 | A | 1/1996 | Goodwin et al. |
| 5,541,158 | A | 7/1996 | Vance et al. |
| 5,559,093 | A | 9/1996 | Yoshitomi et al. |
| 5,661,125 | A | 8/1997 | Strickland |
| 5,716,644 | A | 2/1998 | Zale et al. |
| 6,333,306 | B1 | 12/2001 | Lehmann |
| 6,340,742 | B1 | 1/2002 | Burg et al. |
| 6,548,653 | B1 | 4/2003 | Young et al. |
| 6,583,272 | B1 | 6/2003 | Bailon |
| 7,217,689 | B1 | 5/2007 | Elliott et al. |
| 7,304,150 | B1 | 12/2007 | Egrie et al. |
| 2002/0037841 | A1 | 3/2002 | Papadimitriou |
| 2002/0115833 | A1 | 8/2002 | Burg et al. |

FOREIGN PATENT DOCUMENTS

| AU | A 59145/90 | 1/1991 |
| CA | 2231192 | 3/1998 |
| CA | 2284910 | 9/1999 |
| EP | 0 148 605 A2 | 7/1985 |
| EP | 0 267 678 | 5/1988 |
| EP | 0 357 804 A1 | 3/1990 |
| EP | 0 370 205 B1 | 5/1990 |
| EP | 0 428 267 A2 | 5/1991 |
| EP | 0 640 619 A1 | 3/1995 |
| EP | 0 640 619 B1 | 7/1997 |
| GB | 2171303 | 8/1986 |
| GB | 2172303 | 8/1986 |
| WO | WO 89/03840 | 5/1989 |
| WO | WO 90/14363 | 11/1990 |
| WO | WO 91/05867 | 5/1991 |
| WO | WO 95/05465 | 2/1995 |
| WO | WO 97/09996 A1 | 3/1997 |
| WO | WO 99/02711 | 1/1999 |
| WO | WO 99/11781 | 3/1999 |
| WO | WO 00/24893 | 5/2000 |
| WO | WO 00/61169 | 10/2000 |
| WO | WO 00/67769 | 11/2000 |
| WO | WO 00/67776 | 11/2000 |
| WO | WO 01/03737 | 1/2001 |

OTHER PUBLICATIONS

Houdebine, The methods to generate transgenic animals and to control transgene expression. Journal of Biotechnology, 98:145-160 (2002).*
U.S. Appl. No. 08/479,892, filed Jun. 6, 1995, Elliott et al.
Akahori, H. et al., "The effect of novel erythropoesis stimulating protein (NESP) on anemia induced by renal failure in rats", Exp. Hermatol., 26(8): p. 766 Only (1998). Ashwell et al., "A Protein from Mammalian Liver That Specifically Binds Galactose-Terminated Glycoproteins", Methods Enyzmol., 50: 287-288 (1978).
Boissel et al., "Erythropoietin Structure-Function Relationships", The Biology of Hematopoiesis, pp. 227-232 (1990).
Boissel et al., "Erythropoietin Structure-Function Relationships", J. Biol. Chem., 268: 15983-15993 (1993).
Bontempo, John A., "Formulation Development", Development of Biopharmaceutical Parenteral Dosage Forms, by Marcel Dekker, Inc., Chapter 5, pp. 109-142 (1997).

(Continued)

Primary Examiner — Elizabeth C Kemmerer
Assistant Examiner — Regina M Deberry
(74) Attorney, Agent, or Firm — Robert B. Winter

(57) ABSTRACT

Methods for increasing and maintaining hematocrit in a mammal comprising administering a hyperglycosylated analog of erythropoietin are disclosed. An analog may be administered less frequently than an equivalent molar amount of recombinant human erythropoietin to obtain a comparable target hematocrit and treat anemia. Alternatively, a lower molar amount of a hyperglycosylated analog may be administered to obtain a comparable target hematocrit and treat anemia. Also disclosed are new hyperglycosylated erythopoietin analogs, methods of production of the analogs, and compositions comprising the analogs.

18 Claims, 12 Drawing Sheets

OTHER PUBLICATIONS

Bradford, Marion M., "A Rapid and Sensitive Method for the Quantitation of Microgram Quantities of Protein Utilizing the Principle of Protein-Dye Binding", *Anal. Biochem.*, 72: 248-254 (1976).

Briggs et al., "Hepatic Clearance of Intact and Desialylated Erythropoietin", *Am. J. Physiol.*, 227: 1385-1388 (1974).

Broudy et al., "Recombinant Human Erythropoietin: Purification and Analysis of Carbohydrate Linkage", *Arch. Biochem. Biophys.*, 265: 329-336 (1988).

Burbaum et al., "Understanding Structural Relationships in Proteins of Unsolved Three-Dimensional Structure", *Proteins-Structure, Function and Genetics*, 7(2): 99-111 (1990).

Burnette, W. Neal, "Western Blotting: Electrophoretic Transfer of Proteins from Sodium Dodecyl Sulfate-Polyacrylamide Gels to Unmodified Nitrocellulose and Radiographic Detection with Antibody and Radioiodinated Protein A", *Anal. Biochem.*, 112: 195-203 (1981).

Cheetham et al., "NMR Structure of Human Erythropoietin and a Comparison with its Receptor Bound Conformation", *Nature Structural Biology*, 5(10): 861-866 (1998).

Cheng et. al., "Effective Amplication of Long Targets from Cloned Inserts and Human Genomic DNA", *Proc. Natl. Acad. Sci. USA*, 91: 5695-5699 (1994).

Chern et al., "Structural Role of Amino Acids 99-110 in Recombinant Human Erythropoietin", *Eur. J. Biochem.*, 202: 225-229 (1991).

Chou et al., "Prediction of the Secondary Structure of Proteins from their Amino Acid Sequence", *Adv. Enzymol.*, 47: 45-148 (1978).

Cotes et al., "Bio-Assay of Erythropoietin in Mice Made Polycythaemic by Exposure to Air at a Reduced Pressure", *Nature*, 191: 1065-1067 (1961).

Cunningham et al., "High-Resolution Epitope Mapping of hGH-Receptor Interactions by Alanine-Scanning Mutagenesis", *Science*, 244: 1081-1085 (1989).

DeLorme et al., "Role of Glycosylation on the Secretion and Biological Activity of Erythropoietin", *Biochemistry*, 31: 9871-9876 (1992).

Davis et al., "Characterization of Recombinant Human Erythropoietin Produced in Chinese Hamster Ovary Cells", *Biochemistry*, 26: 2633-2638 (1987).

Dorado et al., "Electrophoretic Behavior of Erythropoietin in Polyacrylamide Gel", *Biochem Medicine*, 6: 238-245 (1972).

Dordal et al., "The Role of Carbohydrate in Erythropoietin Action", *Endocrinology*, 116(6): 2293-2299 (1985).

Dube et al., "Glycosylation at Specific Sites of Erythropoietin is Essential for Biosynthesis, Secretion, and Biological Function", *J. Biol. Chem.*, 263(33): 17516-17521 (1988).

Egrie et al., "Characterization and Biological Effects of Recombinant Human Erythropoietin", *Immunobiol.*, 172: 213-224 (1986).

Egrie et al., "Pharmacokinetics of Recombinant Human Erythropoietin (rHuEpo) Administered to Hemodialysis (HD) Patients", *Kidney intl.*, 33: (Abstract) p. 262 (1988).

Egrie et al., "The Role of Carbohydrate on the Biological Activity of Erythropoietin", *Glycoconjugate J.*, 10: (Abstract S7.7) p. 263 (1993).

Egrie et al, "Novel Erythropoiesis Stimulating Protein (NESP) Has a Longer Serum Half-Life and Greater in vivo Biological Activity than Recombinant Human Erythropoietin (rHuEPO)" *Blood* (Journal of the American Society of Hematology); 90(10) Suppl 1, Part 1; Abstract 243-I, pp. 56a-57a (1997).

Egrie et al., "Development and Characterization of Novel Erythropoiesis Stimulating Protein (NESP)", *British Journal of Cancer*, 84 (suppl. 1): 3-10 (2001).

Egrie et al., "Development and Characterization of Novel Erythropoiesis Stimulating Protein (NESP)", *Nephrology Dialysis Transplantation*, 16(suppl. 3): 3-13 (2001).

Elliott et al., "Characterization of Anti Erythropoietin Monoclonal Antibodies", *Blood*, 74(Supp. 1), A 1228 (1989).

Elliott et al., "Secretion of Glycosylated Human Erythropoietin from Yeast Directed by the *alpha*-Factor Leader Region", *Gene*, 79: 167-180 (1989).

Elliott et al., "An Immunological Approach to Determination of Protein Structure: Human Erythropoietin", *J. Cell. Biochem.*, Supp. 15G: Abstract No. R215, p. 192 (1991).

Elliott et al., "Structural Requirements for O-Linked Glycosylation of Human Erythropoietin", *Abstracts of the Protein Society, 5th Symp*, Abstract No. M43 (1991).

Elliott et al., "Structural Requirements for O-Linked Glycosylation of Human Erythropoietin", Abstract of Presentation at Keystone Symposium, Mar. 21-27, (1992).

Elliott et al., "Effect of Disulfide Bonds on the Structure and Activity of Erythropoietin",*J. Cell. Biochem.*, Supp. 17B,: Abstract No. E318, p. 89 (1993).

Elliott et al, "Structural Requirements for Addition of O-linked Carbohydrate to Recombinant Erythropoietin", *Biochemistry*, 33(37): 11237-11245 (1994).

Elliott et al., "Isolation and Characterization of Conformation Sensitive Antierythropoietin Monoclonal Antibodies: Effect of Disulfide Bonds and Carbohydrate on Recombinant Human Erythropoietin Structure", *Blood*, 87(7): 2714-2722 (1996).

Ellison et al., "The Nucleotide Sequence of a Human Immunoglobulin C$\gamma_1$ Gene", *Nucleic Acids Res.*, 10(13): 4071-4079 (1982).

Emini et al., "Induction of Hepatitis A Virus-Neutralizing Antibody by a Virus-Specific Synthetic Peptide," *J. Virology*, 55(3): 836-839 (1985).

Eschbach et al., "Correction of the Anemia of End-Stage Renal Disease with Recombinant Human Erythropoietin. Results of a Combined Phase I and II Clinical Trial", *New Eng. J. Med.*, 316(2): 73-78 (1987).

Fibi et al, "N- and O-Glycosylation Muteins of Recombinant Human Erythropoietin Secreted from BHK-21 Cells" *Blood*, 85(5): 1229-1236 (1995).

Fischl et al., "Recombinant Human Erythropoietin for Patients with Aids Treated with Zidovudine", *New Eng. J. Med.*, 322(21): 1488-1493 (1990).

Fisher, James W., "Erythropoietin: Physiologic and Pharmacologic Aspects", *Proc. Soc. Exp. Biol. Med.*, 216: 358-369 (1997).

Fu, et al., "The Sheep Erythropoietin Gene: Molecular Cloning and Effect of Hemorrhage on Plasma Erythropoietin and Renal/Liver Messenger RNA in Adult Sheep," *Molecular and Cellular Endocrinology*, 93: 107-116 (1993).

Fuhr et al., "Evaluation of Commercial Erythropoietin Activity after Preparative Isoelectric Focusing", *Biochem. Biophys. Res. Comm.*, 98(4): 930-935 (1981).

Fukuda et al., "Structure and Role of Carbohydrate in Human Erythropoietin," *Adv. Exp. Med. Biol.*, 271: 53-67 (1989).

Fukuda et al., "Survival of Recombinant Erythropoietin in the Circulation: The Role of Carbohydrates", *Blood*, 73(1): 84-89 (1989).

Gallagher et al., "Addition of Carbohydrate Side Chains at Novel Sites on Influenza Virus Hemagglutinin Can Modulate the Folding, Transport, and Activity of the Molecule", *J. Cell Biology*, 107(6, Pt.1): 2059-2073 (1988).

Garnier et al., "Analysis of the Accuracy and Implications of Simple Methods for Predicting the Secondary Structure of Globular Proteins", *J. Mol. Biol.*, 120: 97-120 (1978).

Gavel et al., "Sequence Differences Between Glycosylated and Non-Glycosylated Asn-X-Thr/Ser Acceptor Sites: Implications for Protein Engineering", *Protein Engineering*, 3(5): 433-442 (1990).

Gething et al., "Cell-Surface Expression of Influenza Haemagglutinin from a Cloned DNA Copy of the RNA Gene", *Nature*, 293: 620-625 (1981).

Goldwasser et al., "On the Mechanism of Erythropoietin-induced Differentiation—XIII. The Role of Sialic Acid in Erythropoietin Action", *J. Biol. Chem.*, 249(13): 4202-4206 (1974).

Gross et al., "Cellular trafficking and degradation of erythropoietin and novel erythropoiesis stimulating protein (NESP)", *The Journal of Biological Chemistry*, 281(4): 2024-2032 (2006).

Higuchi, R., "Recombinant PCR" in *PCR Protocols: A Guide to Methods and Applications*, Chapter 22, pp. 177-183 (published by Academic Press, 1990).

Holmes et al., "A Rapid Boiling Method for the Preparation of Bacterial Plasmids", *Anal. Biochem.*, 114: 193-197 (1981).

Imai et al., "Physicochemical and Biological Characterization of Asialoerythropoietin. Suppressive effects on sialic acid in the expression of biological activity of human erythropoietin in vitro", *Eur J. Biochem.*, 194: 457-462 (1990).

Iscove et al., "Erythroid Colony Formation in Cultures of Mouse and Human Bone Marrow: Analysis of the Requirement for Erythropoietin by Gel Filtration and Affinity Chromatography on Agarose-Concanavalin A", *J. Cell Physiol.*, 83: 309-320 (1974).

Jacobs et al., "Isolation and Characterization of Genomic and cDNA Clones of Human eEythropoietin", *Nature*, 313: 806-810 (1985).

Kaufman et al., "Coamplification and Coexpression of Human Tissue-Type Plasminogen Activator and Murine Dihydrofolate Reductase Sequences in Chinese Hamster Ovary Cells", *Mol Cell. Biol.*, 5(7): 1750-1759 (1985).

Kaufman et al., "Transgenic analysis of a 100-kb human B-globin cluster-containing DNA fragment propagated as a bacterial artificial chromosome". *Blood*, 94: 3178-3184 (1999).

Kessler et al., "Structures of N-Glycosidic Carbohydrate Unites of Human chorionic Gonadotropin", *J. Biol. Chem.*, 254: 7901-7908 (1979).

Komatsu et al., "Establishment and Characterization of an Erythropoietin-Dependent Subline, UT-7/Epo, Derived from Human Leukemia Cell Line, UT-7", *Blood*, 82(2): 456-464 (1993).

Krystal et al., "Purification of Human Erythropoietin to Homogeneity by a Rapid Five-Step Procedure," *Blood*, 67(1): 71-79 (1986).

Kunkel et al., "Rapid and Efficient Site-Specific Mutagenesis without Phenotypic Selection", *Methods in Enzymol.*, 154: 367-382 (1987).

Kyngäs et al., "Unreliability of the Chou-Fasman Parameters in Predicting Protein Secondary Structure", *Protein Engineering*, 11(5): 345-348 (1998).

Lai et al., "Structural Characterization of Human Erythropoietin", *J. Biol. Chem.*, 261(7): 3116-3121 (1986).

Laupacis, Dr. Andreas, "Effectiveness of Perioperative Recombinant Human Erythropoietin in Elective Hip Replacement", *Lancet*, 341: 1227-1232 (1993).

Law et al., "Chromosomal Assignment of the Human Erythropoietin Gene and its DNA Polymorphism", *Proc. Natl. Acad. Sci. USA*, 83: 6920-6924 (1986).

Lee et al., "Alteration of Terminal Glycosylation Sequences on N-Linked Oligosaccharides of Chinese Hamster Ovary Cells by Expression of *beta*-Galactoside *alpha*2,6-Sialyltransferase", *J. Biol. Chem.*, 264: 13848-13855 (1989).

Lim, V.I., "Algorithms for Prediction of *alpha*-Helical and *beta*-Structural Regions in Globular Proteins", *J. Mol. Biol.*, 88: 873-894 (1974).

Lin et al., "Cloning and Expression of the Human Erythropoietin Gene", *Proc. Natl. Acad. Sci. USA*, 82: 7580-7584 (1985).

Lin, Fu-Kuen, "The Molecular Biology of Erythropoietin", *Molecular and Cellular Aspects of Erythropoietin & Erythropoiesis*, NATO ASI Series, vol. H8, I.N. Rich., ed., published by Springer-Verlag Berlin Heidelberg, pp. 23-36 (1987).

Lowy et al., "Inactivation of Erythropoietin by Neuraminidase and by Mild Substitution Reactions", *Nature*, 85: 102-103 (1960).

Lukowsky et al., "Studies on the Role of Sialic Acid in the Physical and Biological Properties of Erythropoietin", *Canadian J. Biochem.*, 50: 909-917 (1972).

MacDougall et al., "Comparison of the Pharmacokinetics of Novel Erythropoiesis Stimulating Protein (NESP and Epoetin Alfa (rhEPO) in Dialysis Patients", *J Amer Soc Nephrology*, vol. 8 (Program and Abstracts Issue): Abstract A1233, p. 268A (1997).

MacDougall et al., "Pharmacokinetics of Novel Erythropoiesis Stimulating Protein Compared with Epoetin Alfa in Dialysis Patients", *J Amer Soc Nephrology*, 10(11): 2392-2395 (1999).

MacDougall, I. C., "Novel erythropoesis stimulating protein (NESP) for the treatment of renal anemia", J. Am. Soc. Nephrol., 9: Program and Abstracts Issue, 258A-259A (1998).

Messing, Joachim, "New M13 Vectors for Cloning", *Methods in Enzymol.*, 101: 20-78 (1983).

Mitra et al., "N-linked Oligosaccharides as Outfitter for Glycoprotein Folding, Form and Function", *TRENDS in Biochemical Sciences*, 13(3): 156-163 (2006).

Miyake et al., "Purification of Human Erythropoietin", *J. Biol. Chem.*, 252(15): 5558-5564 (1977).

Morrell et al., "Physical and Chemical Studies on Ceruloplasmin—V. Metabolic Studies on Sialic Acid-Free Ceruloplasmin in vivo", *J. Biol. Chem.*, 243: 155-159 (1968).

Mutsaers et al., "Structural Studies of the Carbohydrate Chains of Human γ-Interferon", *Eur. J. Biochem.*, 156: 651-654 (1986).

Napier, J.A.F., "Isoelectric Focussing of Human Urinary Erythropoietin", *IRCS Med. Sci. Biochem.*, 4: 437 (1976).

Narhi et al., "The Effect of Carbohydrate on the Structure and Stability of Erythropoietin," *J. Biol. Chem.*, 266(34): 23022-23026 (1991).

Papayannopoulou et al., "Globin Phenotypes and Surface Markers of Two New Human Erythroleukemia Lines", *Blood*, 64(supp. 1): (Abstract No. 375) p. 116a (1984).

Phelps et al., "An Electrophoretic and Immunochemical Characterization of Human Surfactant-Associated Proteins", *Biochimica et Biophysica Acta*, 791: 226-238 (1984).

Phillips, A., "The challenge of gene therapy and DNA delivery", J. Pharm. Pharmacology, 53: 1169-1174 (2001).

Pierce et al., "Glycoprotein Hormones: Structure and Function", *Ann. Rev. Biochem.*, 50: 465- 495 (1981).

Quelle et al., "High-Level Expression and Purification of a Recombinant Human Erythropoietin Produced Using a Baculovirus Vector," *Blood*, 74(2): 652-657 (1989).

Radola, Bertold J. ,"IsoElectric Focusing in Layers of Granulated Gels—I. Thin-Layer Isoelectric Focusing of Proteins", *Biochimica et Biophysica Acta*, 295: 412-428 (1973).

Radola, Bertold J., "IsoElectric Focusing in Layers of Granulated Gels—II. Preparative Isoelectric Focusing", *Biochimica et Biophysica Acta*, 386: 181-195 (1974).

Recny et al., "Structural Characterization of Natural Human Urinary and Recombinant DNA-derived Erythropoietin", J. Biol. Chem., 262(35): 17156-17163 (1987).

Rudinger, J., "Characteristics of the Amino Acids as Components of a Peptide Hormone Sequence", *University Park Press*, Baltimore, pp. 1-7 (Jun. 1976).

Sasaki et al., "Carbohydrate Structure of Erythropoietin Expressed in Chinese Hamster Ovary Cells by a Human Erythropoietin cDNA," *J. Biol. Chem.*, 262(25): 12059-12076 (1987).

Sasaki et al., "Site-Specific Glycosylation of Human Recombinant Erythropoietin: Analysis of Glycopeptides or Peptides at Each Glycosylation Site by Fast Atom Bombardment Mass Spectrometry", *Biochemistry*, 27(23): 8618-8626 (1988).

Schneider et al. "Homodimerization of Erythropoietin Receptor by a Bivalent Monoclonal Antibody Triggers Cell Proliferation and Differentiation of Erythroid Precursors," *Blood*, 89(2): 473-482 (1997).

ShakinEshleman, S.H., "Regulation of N-Linked Core-Glycosylation", *Trends in Glycoscience and Glycotechnology*, 8(40): 115-130 (1996).

Shelton et al., "Physicochemical Properties of Erythropoietin: Isoelectric Focusing and Molecular Weight Studies", *Biochem. Med.*, 12: 45-54 (1975).

Strickland, T. W. et al., "Occurrence of Sulfate on the N-Linked Oligosaccharides of Human Erythropoietin", Abstract #P324, p. 167, and Poster at the Keystone Symposium on Glycobiology, (Mar. 1992).

Syed et al., "Efficiency of Signalling Through Cytokine Receptors Depends Critically on Receptor Orientation", *Nature*, 395: 511-516 (1998).

Takeuchi et al., "Sensitive Method for Carbohydrate Composition Analysis of Glycoproteins by High-Performance Liquid Chromatography", *J. Chromatogr.*, 400: 207-213 (1987).

Takeuchi et al., "Comparative Study of the Asparagine-linked Sugar Chains of Human Erythropoietins Purified from Urine and the Culture Medium of Recombinant Chinese Hamster Ovary Cells", *J. Biol. Chem.*, 263: 3657-3663 (1988).

Takeuchi et al., "Relationship Between Sugar Chain Structure and Biological Activity of Recombinant Human Erythropoietin Produced in Chinese Hamster Ovary Cells," *PNAS*, 86: 7819-7822 (1989).

Takeuchi et al., "Role of Sugar Chains in the in Vitro Biological Activity of Human Erythropoietin Produced in Recombinant Chinese Hamster Ovary Cells," *J. Biol. Chem.*, 265: 12127-12130 (1990).

The United States Pharmacopeia (Twenty-First Revision, Official from Jan. 1, 1985) United States Pharmacopeial Convention, Inc. (submitting title page and Reference Table / Pharmaceutic Ingredients, pp. 1491-1493) (1985).

Tsuda et al., "Comparative Structural Study of N-Linked Oligosaccharides of Urinary and Recombinant Erythropoietins," *Biochemistry*, 27: 5646-5654 (1988).

Tsuda et al., "The Role of Carbohydrate in Recombinant Human Erythropoietin," *Eur. J. Biochem.*, 188: 405-411 (1990).

Urlaub et al., "Isolation of Chinese Hamster Cell Mutants Deficient in Dihydrofolate Reductase Activity", *Proc. Natl. Acad. Sci. USA*, 77(7): 4216-4220 (1980).

Vanrenterghem et al., "Novel Erythropoiesis-Stimulating Protein (NESP) Maintains Hemoglobin (Hgb) in ESRD Patients When Administered Once Weekly or Once Every Other Week" *J. Am. Soc. Nephrol.*, vol. 10 (Program and Abstracts Issue-Sep. 1999), Abstract A1365, p. 270A (1999).

Varki, Ajit, "Biological Roles of Oligosaccharides: All of the Theories are Correct," *Glycobiology*, 3(2): 97-130 (1993).

Wang et al., "Rapid analysis of gene expression (RAGE) facilitates universal expression profiling", Nucleic Acids Res., 27(23): 4609-4618 (1999).

Wasley et al., "The Importance of N- and O-Linked Oligosaccharides for the Biosynthesis and In Vitro and In Vivo Biologic Activities of Erythropoietin", *Blood*, 77: 2624-2632 (1991).

Watowich et al., "Activation and Inhibition of Erythropoietin Receptor Function: Role of Receptor Dimerization", *Molecular and Cellular Biology*, 14(6): 3535-3549 (1994).

Webber et al., "Purification of Erythropoietin from Human Urine", *Fedn. Proc.*, 42 (Abstract 672): p. 1872 (1983).

Wells et al., "Cassette Mutagenesis: An Efficient Method for Generation of Multiple Mutations at Defined Sites", *Gene*, 34: 315-323 (1985).

Wells, James A., "Additivity of Mutational Effects in Proteins", *Biochemistry*, 29(37): 8509-8517 (1990).

Wigley et al., "Site-specific transgene insertion: an approach", Reprod. Fertil. Dev., 6: 585-588 (1994).

Yamaguchi et al., "Effects of Site-Directed Removal of N-Glycosylation Sites in Human Erythropoietin on Its Production and Biological Properties", *J. Biol. Chem.*, 266(30): 20434-20439 (1991).

Yanisch-Perron et al., "Improved M13 Phage Cloning Vectors and Host Strains: Nucleotide Sequences of the M13mp18 and pUC19 Vectors", *Gene*, 33: 103-119 (1985).

Zoller et al., "Oligonucleotide-Directed Mutagenesis of DNA Fragments Cloned into M13 Vectors", *Methods in Enzymology*, 100: 468-500 (1983).

Dikov et al., "A Function Fibroblast Growth Factor-1 Immunoglobulin Fusion Protein", *J. Biol. Chem.*, 273(25): 15811-15817 (1998).

Jostock et al, Immunoadhesins of interleukin-6 and the IL-6/soluble IL-6R fusion protein hyper-IL-6, *J. Immunol. Methods*, 223(2): 171-183 (1999).

Yang, J. f., et al., "The EGF-like domain of chick acetylcholine receptor-inducing activity (ARIA) contains its full biological activity", *FEBS Lett.*, 403(2): 163-167 (1997).

* cited by examiner

FIG.1

Met Gly Val His Glu Cys Pro Ala Trp Leu Trp Leu Leu Leu Ser Leu
    -25                  -20                  -15

Leu Ser Leu Pro Leu Gly Leu Pro Val Leu Gly Ala Pro Pro Arg Leu
    -10              -5                   1                   5

Ile Cys Asp Ser Arg Val Leu Glu Arg Tyr Leu Leu Glu Ala Lys Glu
                10                  15                  20

Ala Glu Asn Ile Thr Thr Gly Cys Ala Glu His Cys Ser Leu Asn Glu
                25                  30                  35

Asn Ile Thr Val Pro Asp Thr Lys Val Asn Phe Tyr Ala Trp Lys Arg
        40                  45                  50

Met Glu Val Gly Gln Gln Ala Val Glu Val Trp Gln Gly Leu Ala Leu
    55                  60                  65

Leu Ser Glu Ala Val Leu Arg Gly Gln Ala Leu Leu Val Asn Ser Ser
70                  75                  80                  85

Gln Pro Trp Glu Pro Leu Gln Leu His Val Asp Lys Ala Val Ser Gly
                90                  95                  100

Leu Arg Ser Leu Thr Thr Leu Leu Arg Ala Leu Gly Ala Gln Lys Glu
            105                 110                 115

Ala Ile Ser Pro Pro Asp Ala Ala Ser Ala Ala Pro Leu Arg Thr Ile
            120                 125                 130

Thr Ala Asp Thr Phe Arg Lys Leu Phe Arg Val Tyr Ser Asn Phe Leu
    135                 140                 145

Arg Gly Lys Leu Lys Leu Tyr Thr Gly Glu Ala Cys Arg Thr Gly Asp
150                 155                 160                 165

Arg

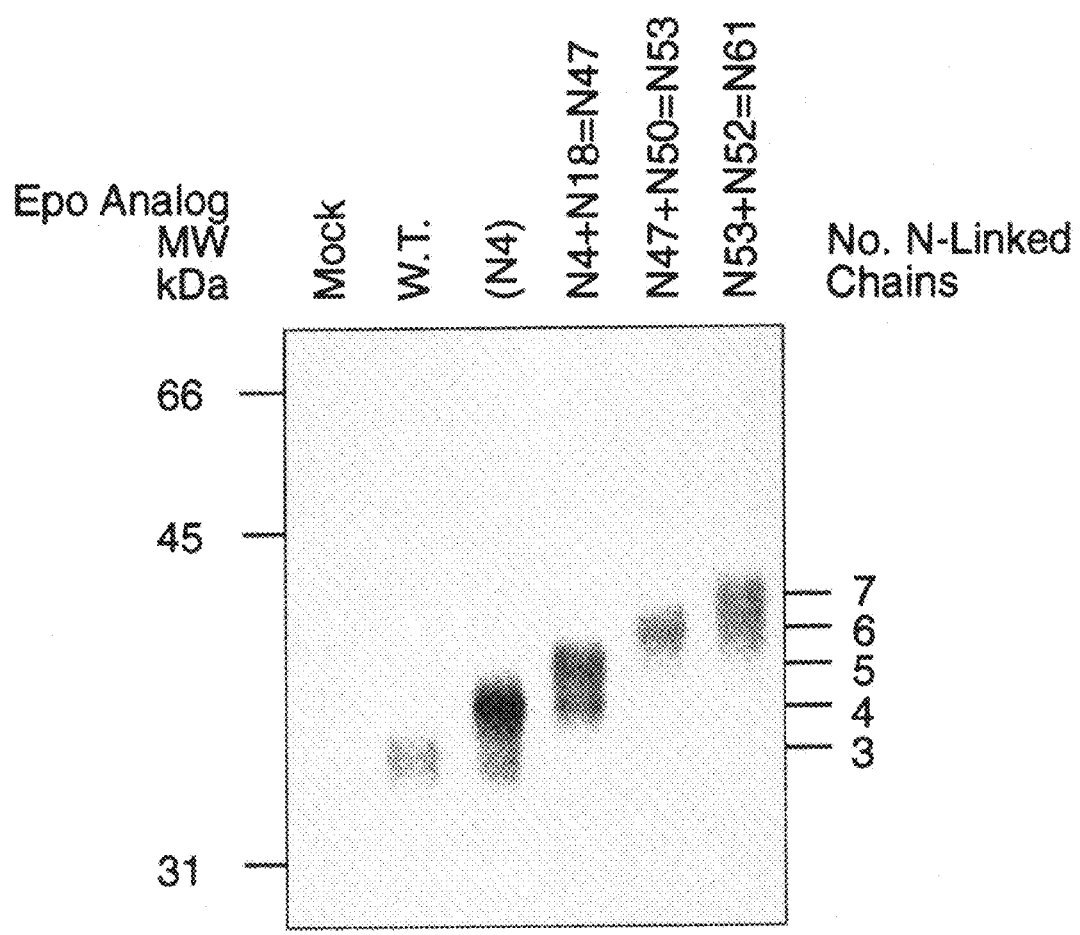

FIG. 10

Amino acid sequence of hinge, CH2 and CH3 regions human IgGγ1

```
Glu Pro Lys Ser Cys Asp Lys Thr His Thr Cys Pro Pro Cys Pro Ala
1             5                   10                  15

Pro Glu Leu Leu Gly Gly Pro Ser Val Phe Leu Phe Pro Pro Lys Pro
         20                  25                  30

Lys Asp Thr Leu Met Ile Ser Arg Thr Pro Glu Val Thr Cys Val Val
         35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
             100                 105                 110

Leu Pro Ala Pro Ile Glu Lys Thr Ile Ser Lys Ala Lys Gly Gln Pro
         115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
             180                 185                 190

Ser Lys Leu Thr Val Asp Lys Ser Arg Trp Gln Gln Gly Asn Val Phe
         195                 200                 205

Ser Cys Ser Val Met His Glu Ala Leu His Asn His Tyr Thr Gln Lys
         210                 215                 220

Ser Leu Ser Leu Ser Pro Gly Lys
225                 230
```

FIG. 11A

```
       aagcttctagaccaccatggggGTGCACGAATGTCCTGCCTGGCTGTGGCTTCTCCTGTC
  1    ---------+---------+---------+---------+---------+---------+  60
       ttcgaagatctggtggtaccccCACGTGCTTACAGGACGGACCGACACCGAAGAGGACAG

M  G  V  H  E  C  P  A  W  L  W  L  L  L  S  -

CCTGCTGTCGCTCCCTCTGGGCCTCCCAGTCCTGGGCGCCCCACCACGCCTCATCTGTGA
  61   ---------+---------+---------+---------+---------+---------+  120
       GGACGACAGCGAGGGAGACCCGGAGGGTCAGGACCCGCGGGGTGGTGCGGAGTAGACACT b      L  L  S  L  P  L  G  L  P  V  L  G  A  P  P  R  L  I  C  D  -

CAGCCGAGTCCTGGAGAGGTACCTCTTGGAGGCCAAGGAGGCCGAGAATATCACGACGGG
 121   ---------+---------+---------+---------+---------+---------+  180
       GTCGGCTCAGGACCTCTCCATGGAGAACCTCCGGTTCCTCCGGCTCTTATAGTGCTGCCC b      S  R  V  L  E  R  Y  L  L  E  A  K  E  A  E  N  I  T  T  G  -

CTGTaatGAAacgTGCAGCTTGAATGAGAATATCACTGTCCCAGACACCAAAGTTAATTT
 181   ---------+---------+---------+---------+---------+---------+  240
       GACAttaCTTtgcACGTCGAACTTACTCTTATAGTGACAGGGTCTGTGGTTTCAATTAAA b      C  N  E  T  C  S  L  N  E  N  I  T  V  P  D  T  K  V  N  F  -

CTATGCCTGGAAGAGGATGGAGGTCGGGCAGCAGGCCGTAGAAGTCTGGCAGGGCCTGGC
 241   ---------+---------+---------+---------+---------+---------+  300
       GATACGGACCTTCTCCTACCTCCAGCCCGTCGTCCGGCATCTTCAGACCGTCCCGGACCG b      Y  A  W  K  R  M  E  V  G  Q  Q  A  V  E  V  W  Q  G  L  A  -

CCTGCTGTCGGAAGCTGTCCTGCGGGGCCAGGCCCTGTTGGTCAACTCTTCCCAGgtgaa
 301   ---------+---------+---------+---------+---------+---------+  360
       GGACGACAGCCTTCGACAGGACGCCCCGGTCCGGGACAACCAGTTGAGAAGGGTCcactt b      L  L  S  E  A  V  L  R  G  Q  A  L  L  V  N  S  S  Q  V  N  - tGAGaCCCTGCAGCTGCATGTGGATAAAGCCGTCAGTGGCCTTCGCAGCCTCACCACTCT
 361   ---------+---------+---------+---------+---------+---------+  420
       aCTCtGGGACGTCGACGTACACCTATTTCGGCAGTCACCGGAAGCGTCGGAGTGGTGAGA b      E  T  L  Q  L  H  V  D  K  A  V  S  G  L  R  S  L  T  T  L  -

GCTTCGGGCTCTGGGAGCCCAGAAGGAAGCCATCTCCCCTCCAGATGCGGCCTCAGCTGC
 421   ---------+---------+---------+---------+---------+---------+  480
       CGAAGCCCGAGACCCTCGGGTCTTCCTTCGGTAGAGGGGAGGTCTACGCCGGAGTCGACG b      L  R  A  L  G  A  Q  K  E  A  I  S  P  P  D  A  A  S  A  A  -

TCCACTCCGAACAATCACTGCTGACACTTTCCGCAAACTCTTCCGAGTCTACTCCAATTT
 481   ---------+---------+---------+---------+---------+---------+  540
       AGGTGAGGCTTGTTAGTGACGACTGTGAAAGGCGTTTGAGAAGGCTCAGATGAGGTTAAA b      P  L  R  T  I  T  A  D  T  F  R  K  L  F  R  V  Y  S  N  F  -

CCTCCGGGGAAAGCTGAAGCTGTACACAGGGGAGGCCTGCAGGACAGGGGACAGAGACAA
 541   ---------+---------+---------+---------+---------+---------+  600
       GGAGGCCCCTTTCGACTTCGACATGTGTCCCCTCCGGACGTCCTGTCCCCTGTCTCTGTT b      L  R  G  K  L  K  L  Y  T  G  E  A  C  R  T  G  D  R  D  K  -

AACTCACACATGTCCACCTTGTCCAGCTCCGGAACTCCTGGGGGGTCCTTCAGTCTTCCT
 601   ---------+---------+---------+---------+---------+---------+  660
       TTGAGTGTGTACAGGTGGAACAGGTCGAGGCCTTGAGGACCCCCCAGGAAGTCAGAAGGA b      T  H  T  C  P  P  C  P  A  P  E  L  L  G  G  P  S  V  F  L  -
```

FIG. 11B

```
            CTTCCCCCCAAAACCCAAGGACACCCTCATGATCTCCCGGACCCCTGAGGTCACATGCGT
        661 ------------+----------+----------+----------+----------+----------+ 720
            GAAGGGGGGTTTTGGGTTCCTGTGGGAGTACTAGAGGGCCTGGGGACTCCAGTGTACGCA b        F  P  P  K  P  K  D  T  L  M  I  S  R  T  P  E  V  T  C  V   -

GGTGGTGGACGTGAGCCACGAAGACCCTGAGGTCAAGTTCAACTGGTACGTGGACGGCGT
        721 ------------+----------+----------+----------+----------+----------+ 780
            CCACCACCTGCACTCGGTGCTTCTGGGACTCCAGTTCAAGTTGACCATGCACCTGCCGCA b        V  V  D  V  S  H  E  D  P  E  V  K  F  N  W  Y  V  D  G  V   -

GGAGGTGCATAATGCCAAGACAAAGCCGCGGGAGGAGCAGTACAACAGCACGTACCGTGT
        781 ------------+----------+----------+----------+----------+----------+ 840
            CCTCCACGTATTACGGTTCTGTTTCGGCGCCCTCCTCGTCATGTTGTCGTGCATGGCACA b        E  V  H  N  A  K  T  K  P  R  E  E  Q  Y  N  S  T  Y  R  V   -

GGTCAGCGTCCTCACCGTCCTGCACCAGGACTGGCTGAATGGCAAGGAGTACAAGTGCAA
        841 ------------+----------+----------+----------+----------+----------+ 900
            CCAGTCGCAGGAGTGGCAGGACGTGGTCCTGACCGACTTACCGTTCCTCATGTTCACGTT b        V  S  V  L  T  V  L  H  Q  D  W  L  N  G  K  E  Y  K  C  K   -

GGTCTCCAACAAAGCCCTCCCAGCCCCCATCGAGAAAACCATCTCCAAAGCCAAAGGGCA
        901 ------------+----------+----------+----------+----------+----------+ 960
            CCAGAGGTTGTTTCGGGAGGGTCGGGGGTAGCTCTTTTGGTAGAGGTTTCGGTTTCCCGT b        V  S  N  K  A  L  P  A  P  I  E  K  T  I  S  K  A  K  G  Q   -

GCCCCGAGAACCACAGGTGTACACCCTGCCCCCATCCCGGGATGAGCTGACCAAGAACCA
        961 ------------+----------+----------+----------+----------+----------+ 1020
            CGGGGCTCTTGGTGTCCACATGTGGGACGGGGGTAGGGCCCTACTCGACTGGTTCTTGGT b        P  R  E  P  Q  V  Y  T  L  P  P  S  R  D  E  L  T  K  N  Q   -

GGTCAGCCTGACCTGCCTGGTCAAAGGCTTCTATCCCAGCGACATCGCCGTGGAGTGGGA
       1021 ------------+----------+----------+----------+----------+----------+ 1080
            CCAGTCGGACTGGACGGACCAGTTTCCGAAGATAGGGTCGCTGTAGCGGCACCTCACCCT b        V  S  L  T  C  L  V  K  G  F  Y  P  S  D  I  A  V  E  W  E   -

GAGCAATGGGCAGCCGGAGAACAACTACAAGACCACGCCTCCCGTGCTGGACTCCGACGG
       1081 ------------+----------+----------+----------+----------+----------+ 1140
            CTCGTTACCCGTCGGCCTCTTGTTGATGTTCTGGTGCGGAGGGCACGACCTGAGGCTGCC b        S  N  G  Q  P  E  N  N  Y  K  T  T  P  P  V  L  D  S  D  G   -

CTCCTTCTTCCTCTACAGCAAGCTCACCGTGGACAAGAGCAGGTGGCAGCAGGGGAACGT
       1141 ------------+----------+----------+----------+----------+----------+ 1200
            GAGGAAGAAGGAGATGTCGTTCGAGTGGCACCTGTTCTCGTCCACCGTCGTCCCCTTGCA

S  F  F  L  Y  S  K  L  T  V  D  K  S  R  W  Q  Q  G  N  V   -

CTTCTCATGCTCCGTGATGCATGAGGCTCTGCACAACCACTACACGCAGAAGAGCCTCTC
       1201 ------------+----------+----------+----------+----------+----------+ 1260
            GAAGAGTACGAGGCACTACGTACTCCGAGACGTGTTGGTGATGTGCGTCTTCTCGGAGAG

F  S  C  S  V  M  H  E  A  L  H  N  H  Y  T  Q  K  S  L  S   -

SalI
                               |
            CCTGTCTCCGGGTAAAtaatgtcgac
       1261 ------------+--------+------ 1286
            GGACAGAGGCCCATTTattacagctg

L  S  P  G  K  *
```

METHODS AND COMPOSITIONS FOR THE PREVENTION AND TREATMENT OF ANEMIA

This application is a divisional of application Ser. No. 11/977,845, filed Oct. 26, 2007, now U.S. Pat. No. 7,973,009 now allowed, which is a divisional of Ser. No. 09/723,955, filed Nov. 27, 2000, issued as U.S. Pat. No. 7,304,150 on Dec. 4, 2007, which is a continuation of Ser. No. 09/559,001, filed Apr. 21, 2000, abandoned, which is a continuation-in-part of Ser. No. 09/178,292, filed Oct. 23, 1998, abandoned, which are hereby incorporated by reference.

FIELD OF THE INVENTION

The invention relates to increasing hematocrit in a mammal using hyperglycosylated analogs of erythropoietin. More particularly, the invention relates to less frequent dosing of a hyperglycosylated analog compared to recombinant human erythropoietin to raise and maintain hematocrit and treat anemia. The invention also relates to administration of lower amounts of a hyperglycosylated analog compared to recombinant human erythropoietin at an equivalent dosing frequency in order to raise and maintain hematocrit and treat anemia. New hyperglycosylated analogs of erythropoietin are also provided.

BACKGROUND OF THE INVENTION

Erythropoietin (Epo) is a glycoprotein hormone necessary for the maturation of erythroid progenitor cells into erythrocytes. It is produced in the kidney and is essential in regulating levels of red blood cells in the circulation. Conditions marked by low levels of tissue oxygen signal increased production of Epo, which in turn stimulates erythropoiesis. A loss of kidney function as is seen in chronic renal failure (CRF), for example, typically results in decreased production of Epo and a concomitant reduction in red blood cells.

Human urinary Epo was purified by Miyake et al. (J. Biol. Chem. 252, 5558 (1977)) from patients with aplastic anemia. However, the amount of purified Epo protein obtained from this source was insufficient for therapeutic applications. The identification and cloning of the gene encoding human Epo and expression of recombinant protein was disclosed in U.S. Pat. No. 4,703,008 to Lin, the disclosure of which is incorporated herein by reference. A method for purification of recombinant human erythropoietin from cell medium is disclosed in U.S. Pat. No. 4,667,016 to Lai et. al., which is incorporated herein by reference. The production of biologically active Epo from mammalian host cells has made available, for the first time, quantities of Epo suitable for therapeutic applications. In addition, knowledge of the gene sequence and the increased availability of purified protein has led to a better understanding of the mode of action of this protein.

Both human urinary derived Epo (Miyake et al. supra) and recombinant human Epo expressed in mammalian cells contain three N-linked and one O-linked oligosaccharide chains which together comprise about 40% of the total molecular weight of the glycoprotein. N-linked glycosylation occurs at asparagine residues located at positions 24, 38 and 83 while O-linked glycosylation occurs at a serine residue located at position 126 (Lai et al. J. Biol. Chem. 261, 3116 (1986); Broudy et al. Arch. Biochem. Biophys. 265, 329 (1988)). The oligosaccharide chains have been shown to be modified with terminal sialic acid residues with N-linked chains typically having up to four sialic acids per chain and O-linked chains having up to two sialic acids. An Epo polypeptide may therefore accommodate up to a total of 14 sialic acids.

Various studies have shown that alterations of Epo carbohydrate chains can affect biological activity. In one study, however, the removal of N-linked or O-linked oligosaccharide chains singly or together by mutagenesis of asparagine or serine residues that are glycosylation sites sharply reduces in vitro activity of the altered Epo that is produced in mammalian cells (Dube et. al. J. Biol. Chem. 263, 17516 (1988)). However, DeLorme et al. (Biochemistry 31, 9871-9876 (1992)) reported that removal of N-linked glycosylation sites in Epo reduced in vivo but not in vitro biological activity.

The relationship between the sialic acid content of Epo and in vivo biological activity was disclosed by determining the in vivo activity of isolated Epo isoforms. It was found that a stepwise increase in sialic acid content per Epo molecule gave a corresponding stepwise increase in in vivo biological activity as measured by the ability of equimolar concentrations of isolated Epo isoforms to raise the hematocrit of normal mice (Egrie et al. Glycoconjugate J. 10, 263 (1993)). Those Epo isoforms having higher sialic acid content also exhibited a longer serum half-life but decreased affinity for the Epo receptor, suggesting that serum half-life is an important determinant of in vivo biological activity.

Introduction of new glycosylation sites in the Epo polypeptide can result in the production of molecules with additional carbohydrate chains. See PCT Publication Nos. WO91/05867 and WO94/09257 hereby incorporated by reference in their entirety. Epo glycosylation analogs having at least one additional N-linked carbohydrate chain and/or having at least one additional O-linked carbohydrate chain are disclosed. A glycosylation analog having one additional N-linked chain was determined to have a longer circulating half-life compared to recombinant human Epo (rHuEpo) (isoforms 9-14) and to a purified isoform of rHuEpo having 14 sialic acids per molecule.

Administration of recombinant human erythropoietin (rHuEpo) is effective in raising red blood cell levels in anemic patients with end stage renal disease (Eschbach et al. New Eng. J. Med. 316, 73-38 (1987)). Subsequent studies have shown that treatment with rHuEpo can correct anemia associated with a variety of other conditions. (Fischl et al. New Eng. J. Med. 322, 1488-1493 (1990); Laupacis, Lancet 341, 1228-1232 (1993). Regulatory approvals have been given for the use of rHuEpo in the treatment of anemia associated with CRF, anemia related to therapy with AZT (zidovudine) in HIV-infected patients, anemia in patients with non-myeloid malignancies receiving chemotherapy, and anemia in patients undergoing surgery to reduce the need of allogenic blood transfusions. Current therapy for all approved indications (except the surgery indication) involves a starting dose of between 50-150 Units/kg three times per week (TIW) administered either by an intravenous (IV) or subcutaneous (SC) injection to reach a suggested target hematocrit range. For the surgery indication, rHuEpo is administered every day 10 days prior to surgery, on the day of surgery, and four days thereafter (EPOGEN® Package Insert, Dec. 23, 1996). In general, the current recommended starting doses for rHuEpo raise hematocrit into the target range in about six to eight weeks. Once the target hematocrit range has been achieved, a maintenance dosing schedule is established which will vary depending upon the patient, but is typically three times per week for anemic patients with CRF. The administration of rHuEpo described above is an effective and well-tolerated regimen for the treatment of anemia.

It would be desirable to have a therapeutic with greater potency than rHuEpo. An advantage to such a molecule would be that it could be administered less frequently and/or at a lower dose. Current treatments for patients suffering from anemia call for administration of EPOGEN® three times per week and for surgery patients administration once per day. A less frequent dosing schedule would be more convenient to both physicians and patients, especially those patients who do not make regularly scheduled visits to doctor's offices or clinics, or those who self-inject their Epo. Another advantage of a more potent molecule is that less drug is being introduced into patients for a comparable increase in hematocrit.

It is therefore an object of the invention to identify more potent molecules for the treatment of anemia which will permit a less frequent dosing schedule. It is a further object of the invention to provide molecules which will increase and maintain hematocrit at levels which are at least comparable to that of Epo when administered at a lower dose. It is also an object of the invention that these molecules selected for less frequent dosing is at least as well tolerated as rHuEpo and potentially better tolerated in some patients.

SUMMARY OF THE INVENTION

It has been found that a hyperglycosylated Epo analog designated N47 ($Asn^{30}Thr^{32}Val^{87}Asn^{88}Thr^{90}Epo$) has a longer serum half-life than recombinant human erythropoietin (rHuEpo) and a greater in vivo activity when administered at the same dose and frequency as rHuEpo. Further, the analog has been shown to raise hematocrit in mice at once per week administration that is comparable to hematocrit rise for rHuEpo administered three times per week. The pharmacokinetics of Epo analog N47 administered to mice and to humans were similar.

The invention provides for a method of raising and maintaining hematocrit in a mammal comprising administering a therapeutically effective amount of an Epo hyperglycosylated analog in a pharmaceutical composition, wherein the analog is administered less frequently than an equivalent molar amount of rHuEpo to obtain a comparable target hematocrit. The dosing frequency of the present invention in order to reach a patient's optimal hematocrit range is less than three times per week. Dosing frequencies may be two times per week, one time per week, or less than one time per week, such as one time every other week, once per month or once every two months. The dosing frequency required to maintain a patient's target hematocrit is less than three times per week. Dosing frequencies may be two times per week, one time per week, or less than one time per week, such as one time every two weeks, once per month or once every two months.

The invention also provides for a method of raising and maintaining hematocrit in a mammal comprising administrating a therapeutically effective amount of an Epo hyperglycosylated analog wherein the analog is administered at a lower molar amount than rHuEpo to obtain a comparable target hematocrit.

Also provided for are pharmaceutical compositions comprising Epo hyperglycosylated analogs wherein the compositions are suitable for dosing frequency of less than three times per week. The compositions will include pharmaceutically acceptable adjuvants suitable for use with Epo hyperglycosylated analogs.

The invention may be employed with any condition resulting in a decrease in red blood cell levels, such as anemia associated with a decline or loss of kidney function, (chronic renal failure) myelosuppressive therapy, cancer, viral infection, chronic disease and excessive loss of blood during surgical procedures. In one embodiment, treatment with once per week dosing, or less frequently, is for anemia resulting from chronic renal failure.

Also provided for are new hyperglycosylated analogs of Epo. The analogs comprise at least one additional carbohydrate chain compared to rHuEpo wherein at least one N-linked carbohydrate chain is added at any of positions 52, 53, 55, 86 and 114. New hyperglycosylated analogs may have two, three or four additional carbohydrate chains, or may have more than four additional chains.

DESCRIPTION OF THE FIGURES

FIG. 1 shows the amino acid sequence of human erythropoietin (SEQ ID NO:1).

FIG. 2 shows a Western blot analysis of rHuEpo and Epo hyperglycosylated analogs from CHO cell expression in serum free medium. Construction of analogs N53 and N61 are described in Example 1. The number of N-linked carbohydrate chains on each analog is indicated.

FIG. 10 shows the amino acid sequence of the hinge, CH2 and CH3 regions of human IgGγ1 (SEQ ID NO: 25).

Figs. 11A and 11B show the cDNA and amino acid sequence of Epo N47-Fc fusion polypeptide including the Epo signal sequence. The amino terminal Fc residue is fused to the arg-166 residue of Epo (SEQ ID Nos: 26 and 27).

DETAILED DESCRIPTION OF THE INVENTION

The invention provides for a method of raising and maintaining hematocrit comprising administering a therapeutically effective amount of a hyperglycosylated analog of erythropoietin in a pharmaceutical composition. The analog is administered less frequently than an equivalent molar amount of rHuEpo to obtain a comparable target hematocrit. The invention also provides for a method of raising and maintaining hematocrit comprising administering a hyperglycosylated analog in lower molar amounts than rHuEpo to obtain a comparable target hematocrit. The composition may be administered by intravenous, subcutaneous or intraperitoneal routes.

Figure 4:
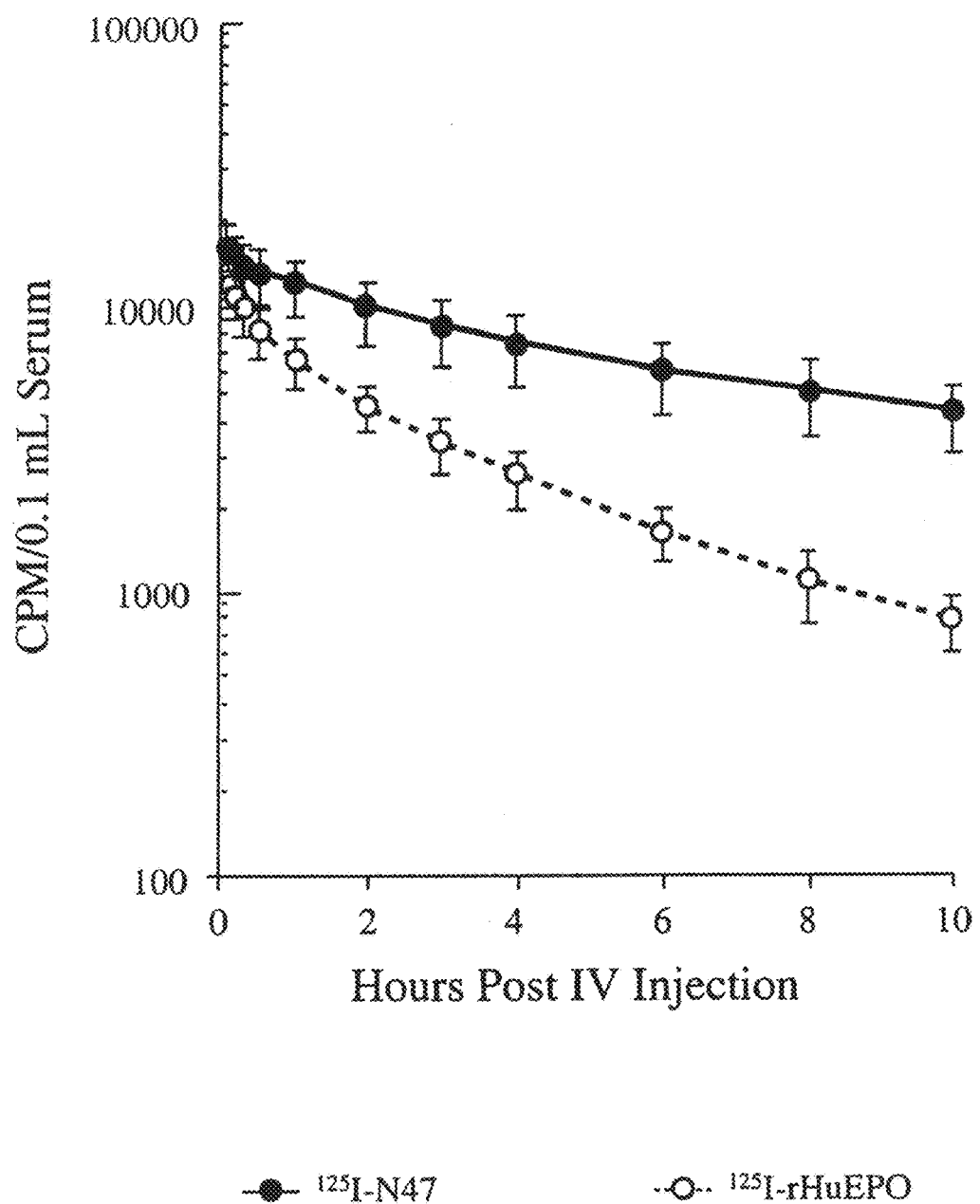
FIG. 4 compares the serum half-life of rHuEpo and Epo analog N47 administered to normal rats by intravenous injection (IV). Experimental procedures are described in Example 4. Results are the mean (±SD) for each group.
Figure 5:
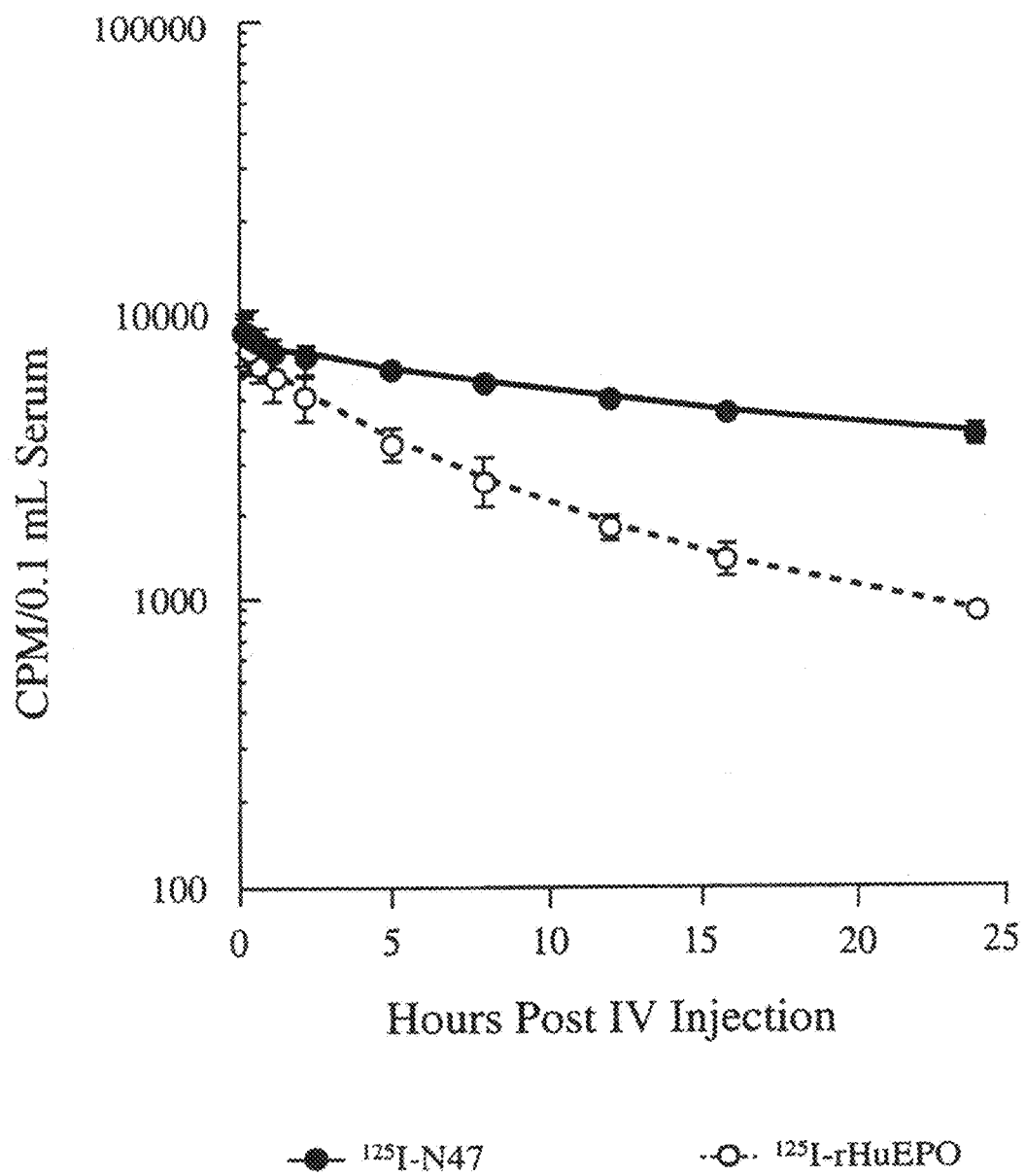
FIG. 5 compares the serum half-life of rHuEpo and Epo analog N47 administered to Beagle dogs by intravenous injection (IV). Experimental procedures are described in Example 4. Results are the mean (±SD) for each group.
Figure 6:
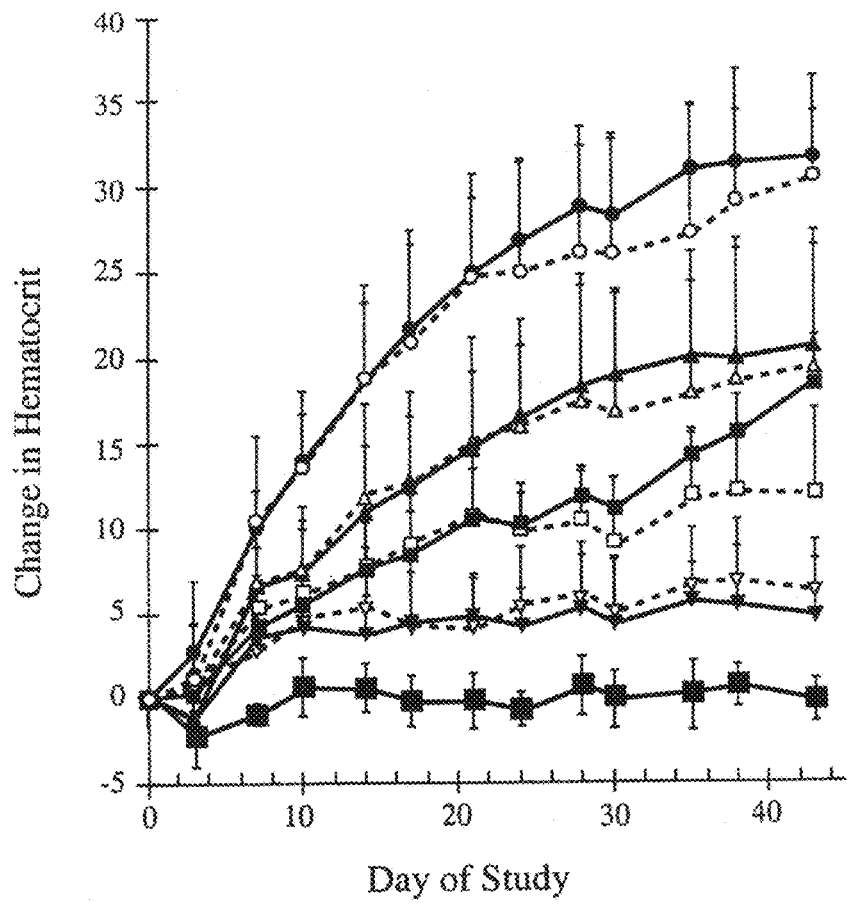
FIG. 6 shows the increase in hematocrit in mice in response to varying doses of rHuEpo or Epo analog N47 administered by intraperitoneal injection (IP) three times per week (TIW) for six weeks. Experimental procedures are described in Example 5. Results shown are the group mean (±SD) of the change in hematocrit for each dose group.
Figure 7:
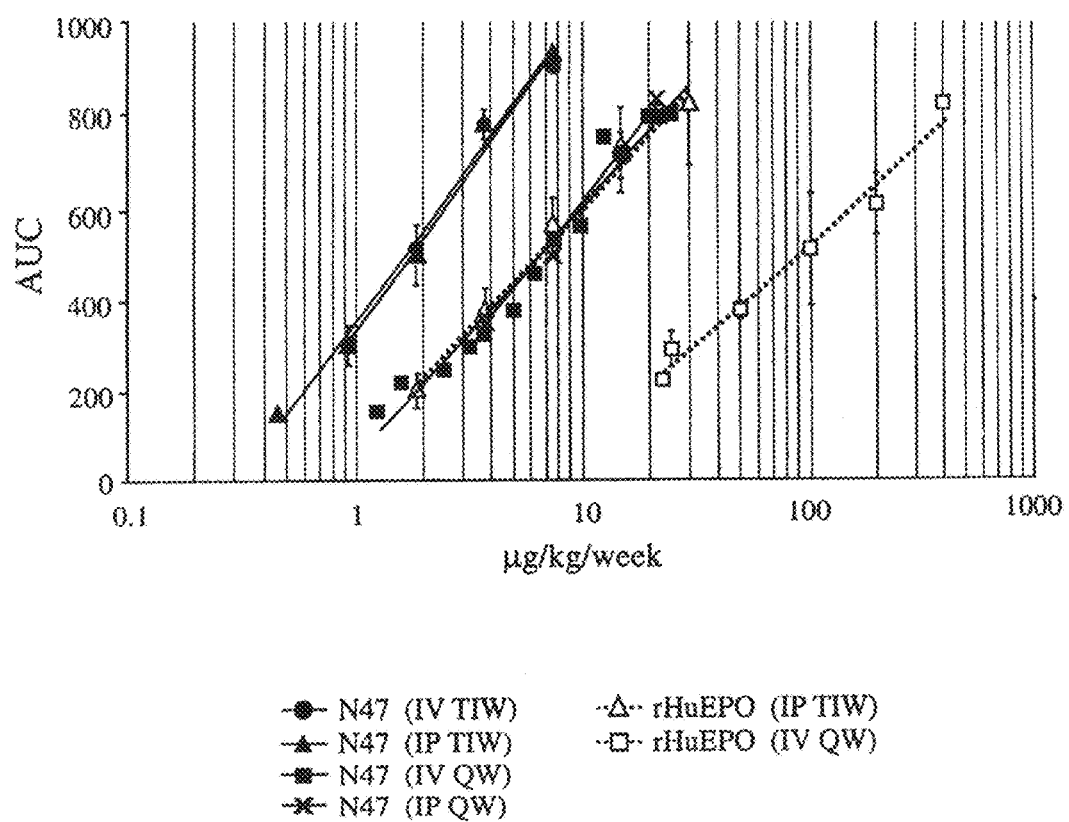
FIG. 7 compares the relative potency in mice of rHuEpo and Epo analog N47 injected by either the intraperitoneal (IP) or intravenous (IV) routes of administration at a frequency of once weekly (QW) or three time a week (TIW). Experimental procedures are described in Example 5. Each point represents the mean (±SD) of data from separate experiments as follows: N47, IP, TIW (n=5); N47, IV, TIW (n=1); N47, IP, QW (n=2); N47, IV, QW (n=3); rHuEpo, IP, TIW (n=5); rHuEpo, IV, QW (n=2). Each experiment used 7-13 mice per dose.
Figure 8:
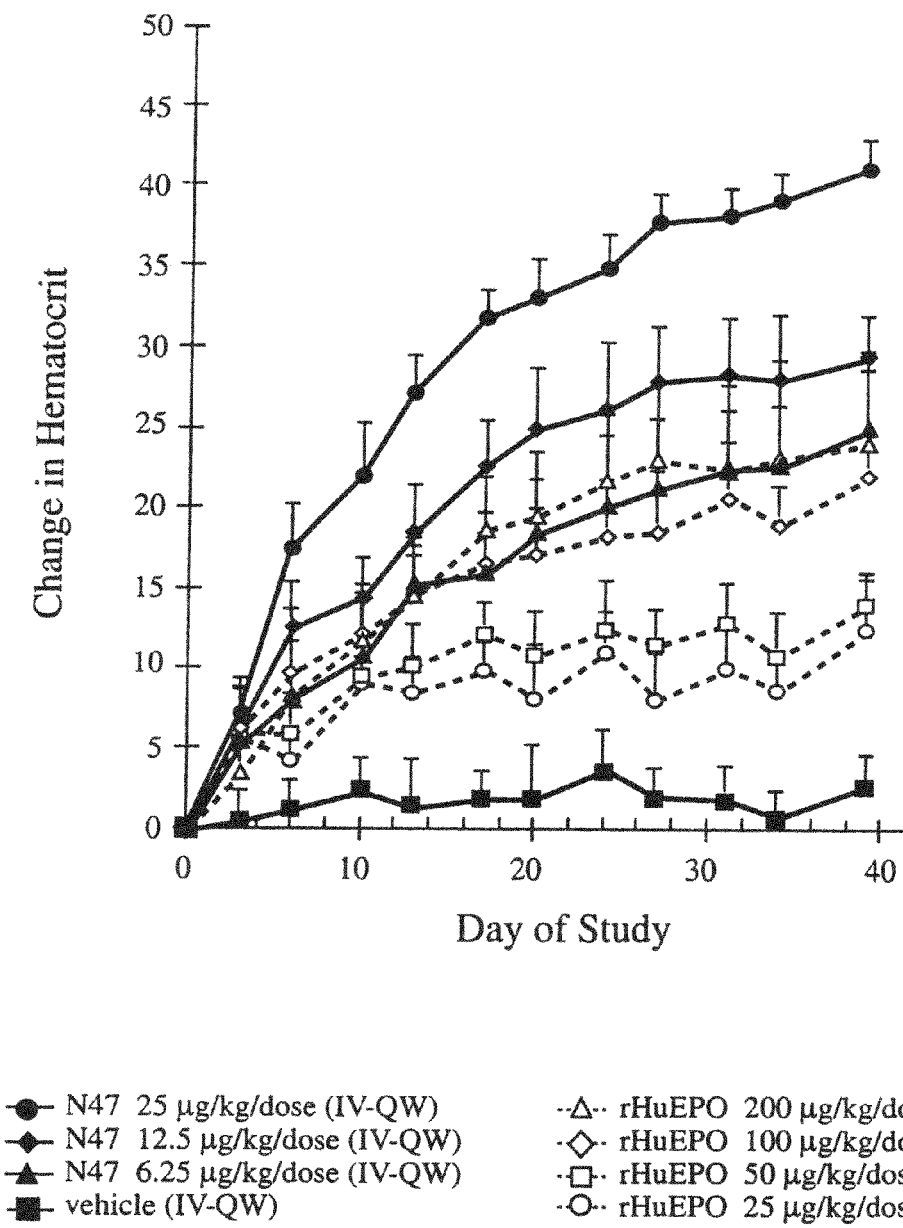
FIG. 8 shows the increase in hematocrit in mice in response to varying doses of rHuEpo or Epo analog N47 administered by intravenous (IV) injection one time per week (QW) for approximately six weeks. Experimental procedures are described in Example 5. Results shown are the group mean (±SD) of the change in hematocrit for each dose group.
Figure 9:
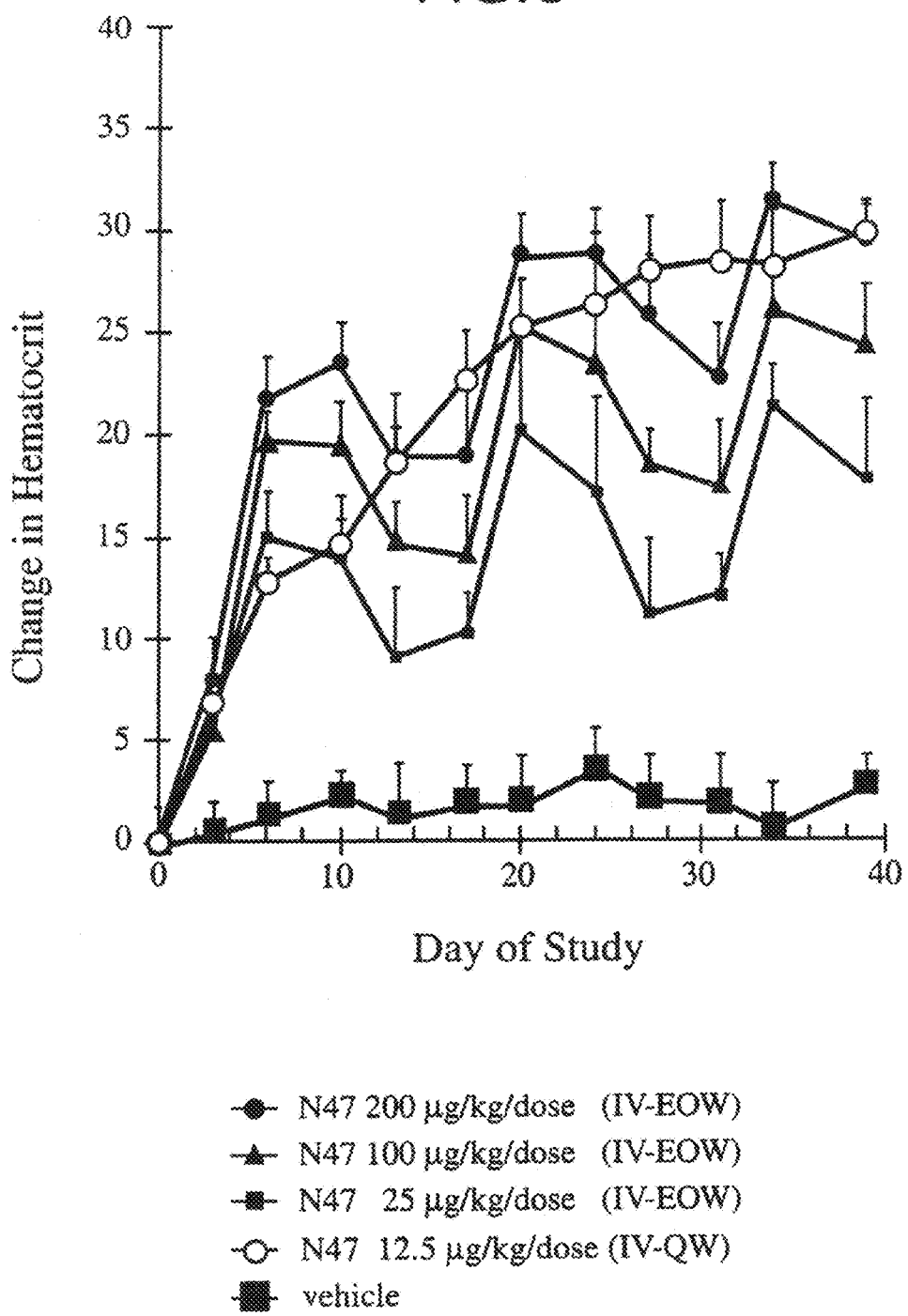
FIG. 9 shows the increase in hematocrit in mice in response to varying doses of Epo analog N47 administered by intravenous (IV) injection one time per week (QW) or once every other week (EOW) for approximately six weeks. Experimental procedures are described in Example 5. Results shown are the group mean (±SD) of the change in hematocrit for each dose group.

Surprisingly, it has been found that analog N47, a hyperglycosylated Epo analog described in WO94/09257, could achieve an increase in hematocrit administered once a week that was comparable to that observed for rHuEpo given three times per week. Analog N47 has the following amino acid changes: ala to asn at 30; his to thr at 32; pro to val at 87; trp to asn at 88; and pro to thr at 90 which resulted in the addition of two N-linked carbohydrate chains at asparagine residues 30 and 88. The analog was expressed in Chinese hamster ovary (CHO) cells (as described in Example 1) and purified as described in Example 2 to give isoforms of 17 to 22 sialic acids. Analog N47 showed a greater serum half-life in rats and beagle dogs than rHuEpo when injected intravenously (FIGS. 4 and 5). When injected intraperitoneally three times per week, N47 induced increases in hematocrit of normal mice comparable to rHuEpo at lower concentrations (FIG. 6). The potency of N47 was demonstrated to be about 3 to 4-fold higher than rHuEpo when administered three times per week (FIGS. 6 and 7). When given once per week, at similar doses, rHuEpo showed little stimulation of hematocrit in normal mice while N47 gave a marked increase (FIG. 8). The potency of N47 was about 14-fold higher than rHuEpo for once per week dosing (FIG. 7). Significantly, the hematocrit response for analog N47 given once per week is comparable to that for rHuEpo given three times per week. Even when administered once every other week, N47 still produced significant increases in the hematocrit of normal mice (FIG. 9). Taken together, the data indicated that Epo hyperglycosylated analogs, and analog N47 in particular, can be used advantageously to raise hematocrit using less frequent dosing than for current treatment with rHuEpo.

It has also been shown that the results described above obtained in mice may be extrapolated to humans. Pharmacokinetic parameters for administration of rHuEpo and analog N47 to 11 Continuous Ambulatory Peritoneal Dialysis (CAPD) patients demonstrate that analog N47 has a three-fold longer serum half-life than rHuEpo (Example 6 and Table 5). These results suggest that Epo hyperglycosylated analogs allow less frequent dosing than rHuEpo in humans.

As used herein, the term "hyperglycosylated Epo analog" refers to Epo comprising at least one additional glycosylation site with an additional carbohydrate chain added to the site. Glycosylation sites may be for N-linked or O-linked carbohydrate chains. New N-linked glycosylation sites are introduced by alterations in the DNA sequence to encode the consensus site for N-linked carbohydrate addition (the amino acids Asn-X-Ser/Thr) in the polypeptide chain, while new O-linked sites are introduced by alterations in the DNA sequence to encode a serine or a threonine residue. The analogs are constructed by mutagenesis techniques for introducing additions, deletions or substitutions of amino acid residues that increase or alter sites in the Epo polypeptide that are available for glycosylation. DNA encoding an Epo hyperglycosylated analog is transfected into a eucaryotic host cell and the expressed glycoprotein is analyzed for the presence of an additional carbohydrate chain.

Epo hyperglycosylated analogs have shown in vitro activity which was comparable to or even less than that determined for rHuEpo, suggesting that binding to the Epo receptor is not enhanced, and may in some cases be diminished, by addition of carbohydrate chains. However, hyperglycosylation can typically increase serum half-life and potentially lead to increased in vivo biological activity. One Epo analog having an additional N-linked carbohydrate chain at position 88 exhibited decreased affinity for receptor compared to rHuEpo (isoforms 9-14) or to a purified isoform of rHuEpo having 14 sialic acids per molecule, yet demonstrated a longer circulating half-life and enhanced in vivo activity compared to either a mixture of Epo isoforms 9-14 or isolated Epo isoform 14.

The Epo hyperglycosylated analogs which may be administered according to the present invention will have at least one additional N-linked or O-linked carbohydrate chain. In one embodiment, the analogs will have two additional N-linked carbohydrate chains. In other embodiments, the analogs will have three, four or more additional N-linked carbohydrate chains. As examples, the analogs of the invention will have at least one additional N-linked chain at one or more of amino acid residues 30, 51, 57, 69, 88, 89, 136 and 138 of the sequence of human Epo. In one embodiment, the analog has additional N-linked carbohydrate chains at residues 30 and 88 of human Epo. The numbering of amino acid residues of human Epo is as shown in FIG. 1 and SEQ ID NO:1. FIG. 1 (SEQ ID NO:1) shows a predicted mature Epo polypeptide of 166 amino acids whereas recombinant produced Epo has 165 amino acids after removal of the C-terminal arginine residue. It is understood that rHuEpo and hyperglycosylated Epo analogs may have either 165 or 166 amino acids.

The analogs of the invention will have at least four N-linked carbohydrate chains. Of the four chains, three may be at the naturally occurring sites at positions 24, 38, and 83. However, it is contemplated that some analogs of the invention may have alterations of one or more of the naturally-occurring glycosylation sites such that one or more of the sites are deleted and substituted with a new site. Such analogs are also provided by the invention. For example, any one of sites at positions 24, 38 and 83 may be deleted and substituted with a site at position 88. Optionally, the analogs may have an O-linked site at position 126.

The invention also provides for new Epo hyperglycosylated analogs having at least one additional carbohydrate chain. It has been found that an additional N-linked carbohydrate chain is added at any of positions 52, 53, 55, 86 and 114 which have been modified to be a glycosylation site. Specific embodiments include analogs N49 through N61 as described in Table 1. The new analogs will have at least one new N-linked glycosylation site at any of positions 52, 53, 55, 86 and 114 and may further comprise additional N-linked or O-linked carbohydrate chains at other sites. The analogs may have one, two, three or four additional carbohydrate chains, or more than four additional chains. In one preferred embodiment, the analogs will have three additional N-linked carbohydrate chains (six N-linked chains total). In another preferred embodiment, the analogs will have four additional N-linked chains (seven N-linked chains total). The analogs having three or four, or more than four, additional N-linked carbohydrate chains may have, but are not limited to, an additional chain at any of positions 52, 53, 55, 86 and 114.

Figure 3:
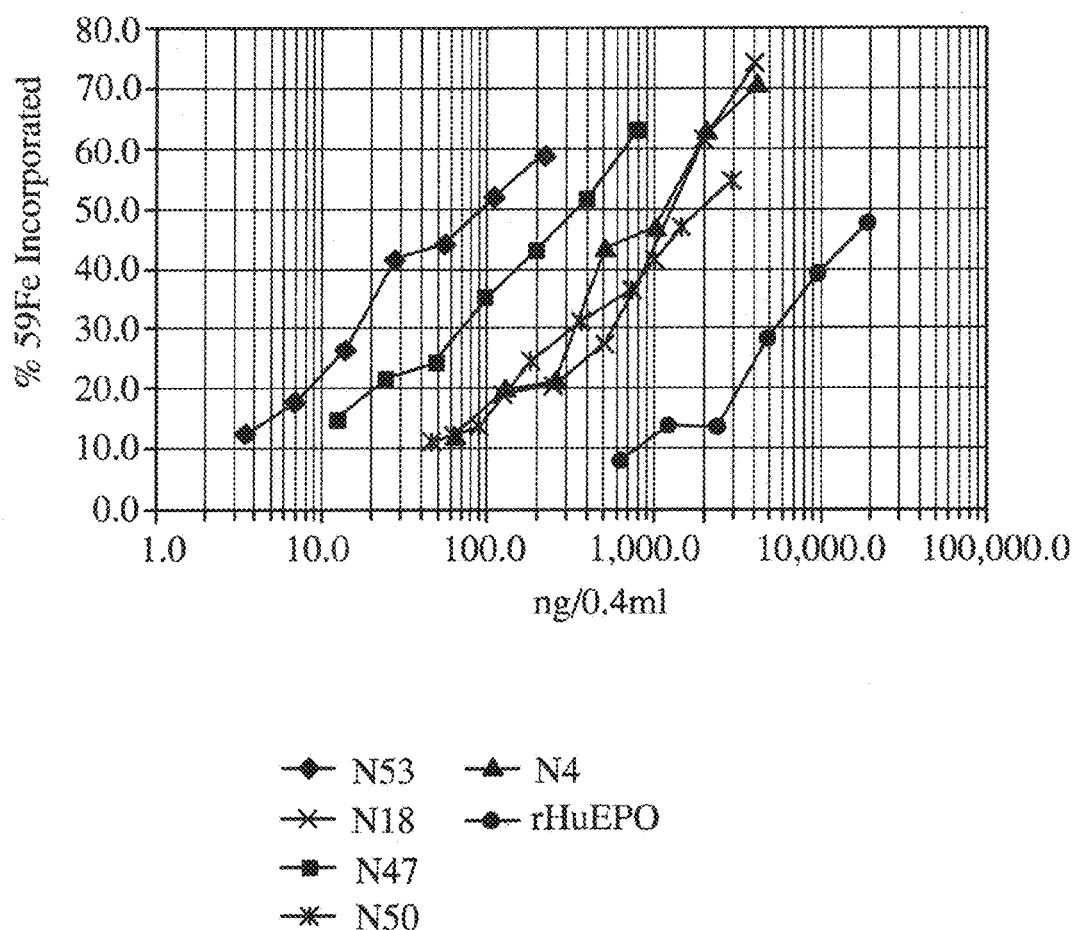
FIG. 3 compares the activity of rHuEpo, Epo analogs N4, N18, and N50 (containing four N-linked carbohydrate chains), N47 (containing five N-linked carbohydrate chains), and N53 (containing six N-linked carbohydrate chains) in the exhypoxic polycythemic mouse bioassay. Experimental procedures are described in Example 3. Each point represents the mean response of five animals. Analogs N4, N18 and N47 have been described previously in WO94/09257.

Surprisingly, it has been found that a hyperglycosylated analog with three additional N-linked chains at positions 30, 53 and 88 (six N-linked chains total) has a greater in vivo activity than analog N47 with two additional chains (five total). The results are shown in FIG. 3. It is clear that the in vivo activity of the analogs is directly dependent on the number of N-linked carbohydrate chains. These results may be extrapolated to the therapeutic setting wherein the analogs having more N-linked carbohydrate chains than N47 may be dosed even less frequently.

In addition, the invention provides for hyperglycosylated Epo analogs with three additional N-linked chains at positions 30, 55 and 88; 30, 55 and 114; and 30, 88 and 114. Epo analogs with four additional N-linked chains or three additional N-linked chains and one additional O-linked chain at position 125 are also provided.

The analogs may be prepared by a variety of mutagenesis techniques available to one skilled in the art, such as site-directed mutagenesis, PCR mutagenesis and cassette mutagenesis (Zoller et al. Meth. Enz. 100, 468-500 (1983); Higuchi, in *PCR Protocols* pp. 177-183 (Academic Press, 1990); Wells et al. Gene 34, 315-323 (1985)). Example 1 describes the use of PCR mutagenesis techniques to construct new Epo hyperglycosylated analogs.

An Epo DNA sequence which has undergone mutagenesis is inserted into an expression vector using standard techniques with the vector being suitable for maintenance in a mammalian host cell. The vector will typically contain the following elements: promoter and other "upstream" regulatory elements, origin of replication, ribosome binding site, transcription termination site, polylinker site, and selectable marker that are compatible with use in a mammalian host cell. Vectors may also contain elements that allow propogation and maintenance in procaryotic host cells as well.

Suitable cells or cell lines include any from mammalian sources, including human sources. Examples include COS-7 (ATCC accession no. CRL 1651), human 293, baby hamster kidney (BHK, ATCC accession no. CCL 10), Chinese hamster ovary cells (including dihydrofolate reductase (DHFR)-deficient cells, Urlab et al. Proc. Natl. Acad. Sci. USA 77, 4216-4220 (1980)) Other suitable mammalian cell lines include, but are not limited to, HeLa, mouse L-929 and 3T3. In a preferred embodiment, DHFR-deficient CHO cells are used.

Vectors comprising sequences encoding Epo hyperglycosylation analogs are introduced into host cells by standard transformation or transfection techniques. Culturing, amplifying and screening transformed or transfected host cells are accomplished using publicly available methods (Gething et al. Nature 293, 620-625 (1981); Kaufman et al. Mol Cell. Biol. 5, 1750-1759 (1985); U.S. Pat. No. 4,419,446). Host cells harboring DNA sequences encoding Epo hyperglycosylated analogs are cultured under conditions that permit expression of the analogs. The analogs are recovered from the cell media and purified using procedures essentially as described previously (WO94/09257) and those in Example 2. The purification procedures allow for the isolation of higher sialic acid containing Epo isoforms resulting from adding additional carbohydrate chains.

The Epo hyperglycosylated analogs may include, in addition to new glycosylation sites, additions, deletions or substitutions of amino acid residues which do not create new glycosylation sites and do not substantially alter the biological activity of the hyperglycosylated analog. Those individual sites or regions of Epo which may be altered without affecting biological activity may be determined by examination of the structure of the Epo-Epo receptor complex as described in Syed et. al. Nature 395, 511 (1998). Examination of the structure of the Epo-Epo receptor complex reveals those residues which interact with, or are in close proximity to, the receptor binding site of Epo and which should be avoided when making alterations in the Epo amino acid sequence. Alternatively, one may empirically determine those regions which would tolerate amino acid substitutions by alanine scanning mutagenesis (Cunningham et al. Science 244, 1081-1085 (1989). In this method, selected amino acid residues are individually substituted with a neutral amino acid (e.g., alanine) in order to determine the effects on biological activity.

It is generally recognized that conservative amino acid changes are least likely to perturb the structure and/or function of a polypeptide. Accordingly, the invention encompasses one or more conservative amino acid changes within an Epo hyperglycosylated analog. Conservative amino acid changes generally involve substitution of one amino acid with another that is similar in structure and/or function (e.g., amino acids with side chains similar in size, charge and shape). The nature of these changes are well known to one skilled in the art and are summarized in Table 1 below. Such conservative substitutions are shown under the heading of "Preferred substitutions". Also contemplated are more substantial changes ("Exemplary substitutions") which may also be introduced. A skilled artisan will appreciate that initially the sites should be modified by substitution in a relatively conservative manner. If such substitutions result in a retention in biological activity, then more substantial changes (Exemplary Substitutions) may be introduced and/or other additions/deletions may be made and the resulting products screened.

TABLE 1

Amino Acid Substitutions

| Original Residue | Preferred Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |
| Ser (S) | Thr | Thr |
| Thr (T) | Ser | Ser |
| Trp (W) | Tyr | Tyr |
| Tyr (Y) | Phe | Trp; Phe; Thr; Ser |
| Val (V) | Leu | Ile; Leu; Met; Phe; Ala; norleucine |

Also provided by the invention are deletions or additions of amino acids in a hyperglycosylated Epo analog which do not substantially affect biological activity. Such additions and deletions may be at the N-terminal or C-terminal of the polypeptide, or may be internal to it. In general, relatively small deletions or additions are less likely to affect structure and/or function of Epo or a hyperglycosylated analog. In one embodiment, deletions or additions can be from 5-10 residues, alternatively from 2-5 amino acid residues, or from 1-2 residues.

The invention provides for fusion proteins comprising Epo hyperglycosylated analogs and compositions thereof. In one aspect, the invention provides for fusion proteins of Epo hyperglycosylated analogs and an immunoglobulin heavy chain constant region. Fusions may be made at the amino terminus of an Epo hyperglycosylated analog, that is, the carboxy terminus of an immunoglobulin heavy chain constant region is fused to the amino terminus of an Epo hyperglycosylated analog. Alternatively, it may be desirable to fuse the carboxy terminus of an Epo hyperglycosylated analog to the amino terminus of an immunoglobulin heavy chain constant region. In one aspect of the invention, the immunoglobulin heavy chain constant region is an Fc region. Epo hyperglycosylated analogs, when part of a fusion polypeptide, may be 165 or 166 amino acids in length, or may have greater or fewer residues if amino acids are added or deleted. In one embodiment, analog N47 is fused at its C-terminus to the N-terminus of an Fc region derived from human IgGγ1. (See Example 2.) In the present example, analog N47 includes the arginine residue at position 166. However, it is contemplated that analog N47 as well as other hyperglycosylated analogs of residues 1-165 (lacking the C-terminal arginine residue) may also comprise the fusion polypeptides of the invention.

The term "Fc" refers to a molecule or sequence comprising the sequence of a non-antigen-binding portion of antibody, whether in monomeric or multimeric form. The original immunoglobulin source of an Fc is preferably of human origin and may be from any isotype, e.g., IgG, IgA, IgM, IgE or IgD. One method of preparation of an isolated Fc molecule involves digestion of an antibody with papain to separate antigen and non-antigen binding portions of the antibody. Another method of preparation of an isolated Fc molecules is production by recombinant DNA expression followed by purification of the Fc molecules so expressed. A full-length Fc consists of the following Ig heavy chain regions: CH1, CH2 and CH3 wherein the CH1 and CH2 regions are typically connected by a flexible hinge region. In one embodiment, an Fc has the amino acid sequence of IgG1 such as that shown in FIG. 10 (SEQ ID NO:25). The terms "Fc protein, "Fc sequence", "Fc molecule", "Fc region" and "Fc portion" are taken to have the same meaning as "Fc".

The term "Fc fragment" when used in association with Fc molecule, or fusion polypeptides thereof, refers to a peptide or polypeptide that comprises less than the full length amino acid sequence of an Fc molecule. Such a fragment may arise, for example, from a truncation at the amino terminus, a truncation at the carboxy terminus, and/or an internal deletion of a residue(s) from the amino acid sequence. Fc fragments may result from alternative RNA splicing or from in vivo protease activity.

The term "Fc variant" when used in association with an Fc molecule, or with fusion polypeptides thereof, refers to a polypeptide comprising an amino acid sequence which contain one or more amino acid sequence substitutions, deletions, and/or additions as compared to native Fc amino acid sequences. Variants may be naturally occurring or artificially constructed. Variants of the invention may be prepared from the corresponding nucleic acid molecules encoding said variants, which have a DNA sequence that varies accordingly from the DNA sequences for native Fc molecule.

The term "derivative" when used in association with an Fc molecule, or with fusion polypeptides thereof, refers to Fc variants or fragments thereof, that have been chemically modified, as for example, by covalent attachment of one or more polymers, including, but limited to, water soluble polymers, N-linked or O-linked carbohydrates, sugars, phosphates, and/or other such molecules. The derivatives are modified in a manner that is different from native Fc, either in the type or location of the molecules attached to the polypeptide. Derivatives further includes deletion of one or more chemical groups naturally attached to an Fc molecule.

The term "fusion" refers to joining of different peptide or protein segments by genetic or chemical methods wherein the joined ends of the peptide or protein segments may be directly adjacent to each other or may be separated by linker or spacer moieties such as amino acid residues or other linking groups.

An Fc, or a variant, fragment or derivative thereof, may be from an Ig class. In one embodiment, an Fc is from the IgG class, such as IgG1, IgG2, IgG3, and IgG4. In another embodiment, an Fc is from IgG1. An Fc may also comprise amino acid residues represented by a combination of any two or more of the Ig classes, such as residues from IgG1 and IgG2, or from IgG1, IgG2 and IgG3, and so forth. In one embodiment, an Fc region of an Epo hyperglycosylated analog fusion protein has the sequence as set forth in FIG. 10 (SEQ ID NO:25) (see Ellison et al., Nucleic Acids Res. 10, 4071-4079 (1982)) starting at residue 6 (that is, residues 1-5 are deleted).

In addition to naturally occurring variations in Fc regions, Fc variants, fragments and derivatives may contain non-naturally occurring changes in Fc which are constructed by, for example, introducing substitutions, additions, insertions or deletions of residues or sequences in a native or naturally occurring Fc, or by modifying the Fc portion by chemical modification and the like. In general, Fc variants, fragments and derivatives are prepared such that the increased circulating half-life of Fc fusions to Epo glycosylation analogs is largely retained.

Also provided by the invention are Fc variants with conservative amino acid substitutions. Examples of conservative amino acid substitutions are set forth hereinabove, and are also exemplified by substitution of non-naturally occurring amino acid residues which are typically incorporated by chemical peptide synthesis rather than by synthesis in biological systems. These include peptidomimetics, and other reversed or inverted forms of amino acid moieties. Conservative modifications to the amino acid sequence of an Fc region (and the corresponding modifications to the encoding nucleotides) are expected to produce Fc molecules (and fusion proteins comprising Epo hyperglycosylated analogs and Fc regions) which have functional and chemical characteristics similar to those of unmodified Fc molecules and fusion proteins comprising unmodified Fc regions.

In addition to the substitutions set forth in Table I, any native residue in an Fc molecule (or in an Fc region of a fusion protein comprising an Epo hyperglycosylated analog) may also be substituted with alanine, as has been previously described for "alanine scanning mutagenesis" (Cunningham et al. Science 244, 1081-1085 (1989)).

Substantial modifications in the functional and/or chemical characteristics of an Fc molecule (and in an Fc region of a fusion protein comprising an Epo hyperglycosylated analog) may be accomplished by selecting substitutions that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain. Naturally occurring residues may be divided into groups based on common side chain properties:

1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Non-conservative substitutions may involve the exchange of a member of one of these classes for a member from another class. Such substituted residues may be introduced into regions of an Fc molecule that are homologous with a non-human Fc molecule, or into the non-homologous regions of the molecule.

Cysteine residues in Fc molecules can be deleted or replaced with other amino acids to prevent formation of disulfide crosslinks. In particular, a cysteine residue at position 5 of FIG. 10 (SEQ. ID. NO:25) may be substituted with one or more amino acids, such as alanine or serine. Alternatively, the cysteine residue at position 5 could be deleted.

An Fc fragment may be prepared by deletion of one or more amino acids at any of positions 1, 2, 3, 4 and 5 as shown in FIG. 10 (SEQ ID NO:25). In one embodiment, the amino acid residues at positions 1-5 inclusive are deleted. Substitutions at these positions can also be made and are with in the scope of this invention.

Fc variants may also be made which show reduced binding to Fc receptors which trigger effector functions such as antibody dependent cellular cytotoxicity (ADCC) and activation of complement (see for example Molec. Immunol. 29, 633-639, (1992)). Such variants may include leucine at position 20 deleted or substituted with a glutamine residue, glutamate at position 103 deleted or substituted with an alanine residue, and lysines at positions 105 and 107 deleted or substituted with alanine residues (following the numbering as set forth in FIG. 1 (SEQ ID NO:1). One or more of such substitutions are contemplated.

In one embodiment, Fc variants will exhibit stronger binding to the FcRn receptor ("salvage receptor") and a longer circulating half-life compared to native Fc such as that shown in FIG. 1 (SEQ ID NO:1). Example of such variants include amino acid substitutions at one or more of residues 33, 35-42, 59, 72, 75, 77, 95-98, 101, 172-174, 215 and 220-223, wherein the substitution(s) confer tighter binding of an Fc variant to the FcRn receptor. In another embodiment, Fc variants have one or more glycosylation sites removed. N-linked glycosylation sites may be removed by deletion or substitution of asparagine residues having attached carbohydrate chains.

Other Fc variants include one or more tyrosine residues replaced with, for example, phenylalanine residues. In addition, other variant amino acid insertions, deletions and/or substitutions are also contemplated and are within the scope of the present invention. Examples include Fc variants disclosed in WO96/32478 and WO97/34630 hereby incorporated by reference. Furthermore, alterations may be in the form of altered amino acids, such as peptidomimetics or D-amino acids.

The Fc protein may be also linked to the Epo glycosylation analogs by "linker" moieties comprising chemical groups or amino acids of varying lengths. Such chemical linkers are well known in the art. Amino acid linker sequences can include but are not limited to:

(a) ala-ala-ala;
(b) ala-ala-ala-ala (SEQ ID NO:6);
(c) ala-ala-ala-ala-ala (SEQ ID NO 7);
(d) gly-gly;
(e) gly-gly-gly;
(f) gly-gly-gly-gly-gly (SEQ ID NO:8);
(g) gly-gly-gly-gly-gly-gly-gly (SEQ ID NO:9);
(h) gly-pro-gly;
(i) gly-gly-pro-gly-gly (SEQ ID NO:10); and
(j) any combination of subparts (a) through (i).

While Fc molecules are preferred as components of fusion proteins with Epo glycosylation analogs, it is also contemplated that other amino acid sequences which bind to an FcRn receptor and confer increased in vivo half-life may also be used. Examples of such alternative molecules are described in U.S. Pat. No. 5,739,277, issued Apr. 14, 1998 to Presta et al.

The term "molar amount" refers to an amount of a hyperglycosylated analog or rHuEpo which is based upon the molecular weight of the corresponding erythropoietin polypeptide without glycosylation. Equivalent amounts of rHuEpo and analog refer to amounts which are equal when taking into account normal variations in procedure used to determine such amounts. It is necessary to determine equivalent amounts in this manner since the molecular weight of rHuEpo and analogs will vary depending upon the number of carbohydrate chains. For rHuEpo, the molecular weight of erythropoietin polypeptide is calculated based upon amino acid residues 1-165 as shown in FIG. 1 and SEQ ID NO: 1. For hyperglycosylated analogs, the molecular weights are adjusted depending upon the amino acid changes in residues 1-165 of FIG. 1 and SEQ ID NO: 1.

The dosing frequency for a hyperglycosylated analog will vary depending upon the condition being treated and the target hematocrit, but in general will be less than three times per week. The dosing frequency will be about two times per week, about one time per week. The dosing frequency may also be less than about one time per week, for example about one time every two weeks(about one time per 14 days), one time per month or one time every two months. It is understood that the dosing frequencies actually used may vary somewhat from the frequencies disclosed herein due to variations in responses by different individuals to the Epo analogs; the term "about" is intended to reflect such variations.

As used herein, the term "therapeutically effective amount" refers to an amount of a hyperglycosylated analog (or a fusion protein comprising an Epo hyperglycosylated analog and an immunoglobulin heavy chain constant region) which gives an increase in hematocrit to a target hematocrit, or to a target hematocrit range that provides benefit to a patient or, alternatively, maintains a patient at a target hematocrit, or within a target hematocrit range. The amount will vary from one individual to another and will depend upon a number of factors, including the overall physical condition of the patient, severity and the underlying cause of anemia and ultimate target hematocrit for the individual patient. A target hematocrit is typically at least about 30%, or in a range of 30%-38%, preferably above 38% and more preferably 40%-45%. General guidelines relating to target hematocrit ranges for rHuEpo are also found in the EPOGEN® package insert dated Dec. 23, 1996 and are 30%-36%, or alternatively 32%-38% as stated therein. It is understood that such targets will vary from one individual to another such that physician discretion may be appropriate in determining an actual target hematocrit for any given patient. Nonetheless, determining a target hematocrit is well within the level of skill in the art.

A therapeutically effective amount of the present compositions may be readily ascertained by one skilled in the art.

Example 6 sets forth a clinical protocol which has as one objective to determine a therapeutically effective amount of analog N47 in both once per week and three times per week dosing. A dose range for once per week administration is from about 0.075 to about 4.5 μg erythropoietin peptide per kg per dose. A dose range for three times per week administration is 0.025 to 1.5 μg erythropoietin peptide per kg per dose. This dose range may be employed with other Epo hyperglycosylated analogs, with any adjustments in the dosing range being routine to one skilled in the art.

A significant advantage to the present invention is the ability to correlate the extent of hyperglycosylation either with a dose amount or with a dosing interval that would allow one to "tailor" an Epo analog to a given dose or dosing schedule. Based upon the increasing in vivo activities of Epo analogs having one, two or three additional carbohydrate chains as shown in FIG. 3, the treating physician can select an analog that is appropriate and convenient for the anemic condition being treated. For example, in patients who are acutely anemic and in need of a large effective dose, or in patients which require a longer-lasting treatment, administration of a hyperglycosylated analog with three or four or even more additional carbohydrate chains may be preferred. For other patients who experience less severe anemia or require treatment for a relatively short time, an analog with one or two additional carbohydrate chains may be preferred. The analogs of the present invention provide the physician with considerable flexibility in preventing and treating anemia that may result from a wide variety of underlying conditions.

The invention also provides for administration of a therapeutically effective amount of iron in order to maintain increased erythropoiesis during therapy. The amount to be given may be readily determined by one skilled in the art based upon therapy with rHuEpo.

The present invention may be used to stimulate red blood cell production and prevent and treat anemia. Among the conditions treatable by the present invention include anemia associated with a decline or loss of kidney function (chronic renal failure), anemia associated with myelosuppressive therapy, such as chemotherapeutic or anti-viral drugs (such as AZT), anemia associated with the progression of non-myeloid cancers, anemia associated with viral infections (such as HIV), and anemia of chronic disease. Also treatable are conditions which may lead to anemia in an otherwise healthy individual, such as an anticipated loss of blood during surgery. In general, any condition treatable with rHuEpo may also be treated with the Epo hyperglycosylated analogs of the invention.

The invention also provides for pharmaceutical compositions comprising a therapeutically effective amount of an Epo hyperglycosylated analog, together with a pharmaceutically acceptable diluent, carrier, solubilizer, emulsifier, preservative and/or adjuvant. The invention also provides for a pharmaceutical composition comprising a therapeutically effective amount of a fusion protein comprising an Epo hyperglycosylated analog and an immunoglobulin heavy chain constant region together with a pharmaceutically acceptable diluent, carrier, solubilizer, emulsifier, preservative and/or adjuvant. The composition will be suitable for a dosing schedule of less than three times per week. The composition may be in a liquid or lyophilized form and comprises a diluent (Tris, citrate, acetate or phosphate buffers) having various pH values and ionic strengths, solubilizer such as Tween or Polysorbate, carriers such as human serum albumin or gelatin, preservatives such as thimerosal, parabens, benzylalconium chloride or benzyl alcohol, antioxidants such as ascrobic acid or sodium metabisulfite, and other components such as lysine or glycine. Selection of a particular composition will depend upon a number of factors, including the condition being treated, the route of administration and the pharmacokinetic parameters desired. A more extensive survey of components suitable for pharmaceutical compositions is found in *Remington's Pharmaceutical Sciences,* 18th ed. A. R. Gennaro, ed. Mack, Easton, Pa. (1980). In a preferred embodiment, the Epo glycosylation analogs of the invention are formulated in liquid form in an isotonic sodium chloride/sodium citrate buffered solution containing human albumin, and optionally containing benzyl alcohol as a preservative. The compositions preferably contain analogs having one, two, three, four, or more additional carbohydrate chains.

Compositions of the invention are preferably administered by injection, either subcutaneous or intravenous. The route of administration eventually chosen will depend upon a number of factors and may be ascertained by one skilled in the art.

The following examples are offered to more fully illustrate the invention, but are not to be construed as limiting the scope thereof.

EXAMPLE 1

Construction of Hyperglycosylated Epo Analogs

Construction of cDNAs Encoding Hyperglycosylated Epo Analogs

Epo analogs were made by in vitro mutagenesis using several different methods. Analogs N49 and N50 were constructed as described in WO94/09257. Analogs were also constructed by variations of overlap PCR (polymerase chain reaction) methods. The basic procedure included two successive steps. In the first step, two reactions (PCR1 and PCR2) were performed on Epo or Epo analog template DNA using a total of four oligonucleotides: a 5' (forward) primer, a reverse mutagenic primer, a forward mutagenic primer (usually complementary to the reverse mutagenic primer) and a 3' (reverse) primer. The mutagenic primers contained the desired nucleotide changes as well as 6-14 exact match nucleotides on each side of these changes. PCR1 used the 5' (forward) primer and the reverse mutagenic primer. PCR2 used the 3' (reverse) primer and the forward mutagenic primer. The amplified DNA fragments were separated by agarose gel electrophoresis. Small pieces of agarose containing DNA fragments of the correct size were excised from the gel. The DNA fragments from PCR1 and PCR2 were combined together and a third PCR reaction was performed using only the 5' forward and 3' reverse primers. Thus, a full length DNA segment containing the desired mutations was amplified. In several cases, two or three mutations were combined by introducing a new substitution into DNA already containing a change, using the same PCR process. To construct these multiple glycosylation site analogs, single double or triple site analogs (produced as described above) were used as PCR template, and an additional glycosylation site was introduced by site directed mutagenesis with the appropriate primers.

The Epo analogs N51, N52 and N53 were constructed by the overlap PCR (polymerase chain reaction) method 1. One additional N-glycosylation site was introduced in each case. N56 added a glycosylation site (N114 T116) to native sequence HuEpo by using pDSRα2 Epo as PCR template, N51 added an O-linked glycosylation site (Thr125) to N47 Epo by using pDSRα2 Epo N47 template (Asn30, Thr32, Val87, Asn88, Thr90) and analog N59 added a glycosylation site (Asn53) to analog N47 using pDSRα2 EpoN47 template.

Polymerase chain reactions for method 1 were performed using a protocol adapted from Cheng et. al., (Proc. Natl. Acad.

Sci. USA 91, 5695 (1994)). The 3' (reverse) primer contained sequences that introduced a stop codon followed by a Xba I restriction site:

ATCTAGAAGTTGCTCTCTGGACAGTTCCT.    (SEQ ID NO: 2)

The 5' forward reaction primer:

GAAGCTTGCGCCACCATGGGGGTGCACGAATG    (SEQ ID NO: 3)

had an Hind III restriction site followed by a Kozak sequence upstream of the Epo initiator codon (ATG). The typical PCR reaction mix contained: 4 µl each of forward and reverse primers (5 pmol/µl), 1 µl template (25 ng), 10 µl of 5× LP buffer (100 mM Tricine pH 8.7/25% glycerol/425 mM KOAc), 10 µl dNTP stock (1 mM each of dATP, dTTP, dCTP, dGTP), 0.8 µl rtTh polymerase (Perkin Elmer; 2.5 U/µl), and 2 µl Vent polymerase (NEB; 0.01 U/µl after 1:100 fresh dilution in 1×LP buffer). H$_2$O was added to bring the final volume to 50 µl. All the components were added together in the order shown and the PCR was started when the temperature during the first cycle was above 60° C. by adding 1 µl of 50 mM MgOAc. Typical reaction conditions were: 2 cycles of 94° C., 10 sec/50° C., 1 min./68° C., 5 min. followed by 25 cycles of 94° C., 10 sec/55° C., 1 min./68° C., 5 min. The amplified fragments were separated by agarose gel electrophoresis and the correct sized DNA fragment was purified using a Geneclean™ kit and procedures supplied by the manufacturer (Bio 101, Inc.). The purified DNA was digested with Hind III and Xba I, then it was purified again using the Geneclean™ kit. The fragment was then ligated into Hind III and Xba I cut pDSRα2 vector. Ligated DNA was precipitated with 2 volumes of ethanol in 0.3M NaOAc pH 5.2 in the presence of carrier tRNA and transformed into E. coli. Epo analogs were screened by restriction digest on mini DNA preps. Plasmids from positive clones were then prepared and the insert was sequenced to confirm the presence of the desired mutations and to ensure that no additional amino acid changes were introduced.

Analogs N54 to N61 were constructed using overlap PCR strategy method 2. The 3'(reverse) primer contained sequences that introduced a stop codon followed by a XbaI restriction site:

GATCCTCTAGAGTTGCTCTCTGGACAG.    (SEQ ID NO: 4)

The 5' forward reaction primer:

CAACAAGCTTGCGCCGCCATGGGGG    (SEQ ID NO: 5)

had a HindIII restriction site followed by a Kozak sequence upstream of the Epo initiator codon (ATG). A high fidelity PCR strategy was performed using Perkin Elmer UlTma DNA Polymerase and accompanying reagents; 10 µl 10× PCR buffer, 3 µl 1 mM dNTPs, 5 pmol of each primer, and water in a final volume of 100 µl. 0.5 units of UlTma polymerase was added after the PCR mixture reached 94° C. PCR reactions were then carried out for 5 cycles at 94° C. for 30 seconds, 50° C. for 30 seconds, and 72° C. for 90 seconds. A subsequent 25 cycles were performed at 94° C. for 30 seconds, and 72° C. for 90 seconds. Product bands of the correct sizes were excised from an agarose gel following electrophoresis.

The resulting PCR products for each analog were cleaned using the Qiagen gel extraction kit. The purified DNA was digested in a 100 µl restriction digest with HindIII and XbaI restriction enzymes (Boehringer Mannheim) at 37° C. for 1 hour. The digests were again gel purified and the digested fragment was then ligated into HindIII and XbaI digested pDSRa2 vector.

Ligated DNA was precipitated with 2 volumes of ethanol in 0.3M NaOAc pH 5.2 in the presence of carrier tRNA and transformed into E. coli. Epo hyperglycosylated analogs were initially screened by colony PCR to identify clones containing the correctly sized and type of DNA insert. With this procedure, cells containing plasmids were placed into PCR tubes in the presence of Epo forward and reverse primers. The mixture was then subjected to PCR using the reaction conditions described above. Plasmids from positive clones were then prepared and the Epo analog insert was sequenced to confirm the presence of the desired mutations and to ensure that no additional amino acid changes were introduced.

TABLE 1

ERYTHROPOIETIN ANALOGS HAVING SITES FOR N-LINKED CARBOHYDRATE CHAINS

| Analog | Amino Acid Substitution | Sequence Changes |
|---|---|---|
| N49 | Lys, Met→Asn52, Thr54 | AAG, ATG→AAT, ACC |
| N50 | Arg, Glu→Asn53, Thr55 | AGG, GAG→AAT, ACG |
| N51 | Ala, His, Pro, Trp, Pro, Ala→ N30, T32, V87, N88, T90 T125 | GCT, CAC, CCG, TGG, CCC, GCC→AAT, ACG, GTG, AAT, ACC, ACC |
| N52 | Ala, Lys→Asn114, Thr116→ | GCC, AAG→AAC, ACG |
| N53 | Ala, His, Arg, Glu Pro, Trp, Pro→ N30, T32, N53, T55, V87, N88, T90 | GCT, CAC, AGG, GAG, CCG, TGG, CCC→AAT, ACG, AAT, ACG, GTG, AAT, ACC |
| N54 | Glu, Gly→Asn55, Thr57 | GAG, GGG→AAT, ACT |
| N55 | Gln, Pro, Trp→Asn86, Val87, Thr88 | CAG, CCG, TGG→ACC, GTG, ACG |
| N56 | Pro, Trp, Pro→Ala87, Asn88, Thr90 | CCG, TGG, CCC→GCG, AAT, ACC |
| N57 | Pro, Trp, Pro→Val87, Asn88, Ser90 | CCG, TGG, CCC→GTG, AAT, ACG |

TABLE 1-continued

ERYTHROPOIETIN ANALOGS HAVING SITES
FOR N-LINKED CARBOHYDRATE CHAINS

| Analog | Amino Acid Substitution | Sequence Changes |
|---|---|---|
| N58 | Pro, Trp, Glu, Pro→<br>Val87, Asn88, Gly89, Thr90 | CCG, TGG, GAG, CCC→<br>GTG, AAT, GGG, ACC |
| N59 | Ala, His, Arg, Glu→<br>Asn30, Thr32, Asn53, Asn55 | GCT, CAC AGG GAG→<br>AAT, ACG, AAT, ACG |
| N60 | Ala, His, Ala, Lys→<br>Asn30, Thr32, Asn114, Thr116 | GCT, CAC, GCC, AAG→<br>AAT, ACG, AAC, ACG |
| N61 | A, H, R, E, P, W, P, A, K→<br>N30, T32, N53, T55, V87, N88,<br>T90, N114, T115 | GCT, CAC, ACG, GAG, CCG,<br>TGG, CCC, GCC, AAG→AAT, ACG, AAT,<br>ACG, GTG, AAT, ACC, AAC, ACG |

Analysis of Carbohydrate Addition

The constructs for the hyperglycosylated Epo analogs which were inserted into the expression vector pDSRα2 were transfected into COS cells. Supernatants from the transfected COS cells were analyzed by western blot to determine whether the expressed and secreted Epo analog contained additional carbohydrate. Samples were loaded directly into wells of SDS-PAGE gels then analyzed by immunoblot using the monoclonal antibody, 9G8A (Elliott et al (1996) Blood 87:p2714). Mobilities of analog samples were compared to that of samples containing rHuEpo. FIG. 1 (SEQ ID NO:1) shows decreased mobility of analogs N53 and N61 compared to analogs N4 (four carbohydrate chains) and N47 (five carbohydrate chains). The mobility is consistent with the presence of six carbohydrate chains for analog N53 and seven carbohydrate chains for analog N61. Data for all hyperglycosylated analogs are shown in Table 2.

In Vitro Bioassays

Media conditioned by COS or CHO cells expressing rHuEpo or analogs were assayed for stimulation of 3H-thymidine uptake by UT7-Epo cells (Komatsu et al., Blood 82,456). UT7-Epo cells are responsive to Epo and express human Epo receptors on their cell surface. UT7-Epo cells were grown in Growth medium (1× Iscove's Modified Dulbecco's Medium with L-glutamine, 25 mM HEPES buffer, and 3024 mg/L sodium bicarbonate, but without either alpha-thioglycerol or beta-mercaptoethanol (GIBCO)/10% v/v Fetal Bovine Serum/1% v/v L-glutamine-Penicillin-Streptomycin solution (Irvine Scientific)/1 Unit/mL rHuEpo) to approximately $3\times10^5$ cells/mL. Cells were collected by centrifugation (approx. 500×G) washed twice with phosphate buffered saline and resuspended at $5\times10^4$ cells/mL in Assay medium (1× RPMI Medium 1640 without L-glutamine (Gibco)/1% L-glutamine/4% fetal bovine serum). Test samples or Epo standard (rHuEpo), 100 uL diluted in assay medium at least 5-fold, were added to wells in a 96 well microtiter plate. 50 µL of suspended cells were then added (5000 cells/well) and plates were incubated in a humidified incubator at 37° C. and 5% $CO_2$. After 72 hours, 50 uL methyl-$^3$H-Thymidine (1 mCi/mL; 20 Ci/mMole) diluted 1:100 in assay medium was added. Cells were incubated for an additional 4 hours at 37° C. and 5% $CO_2$. Labeled cells were harvested onto glass fiber filtermats, washed with deionized water followed by 2-propanol, dried and counted. Activity was determined by comparing the response determined for each analog to that of the rHuEpo standard. The specific biological activity was then determined by dividing in vitro activity by the concentration of each analog as determined by immunoassay (Elliott et al (1996) Blood 87:p 2714). The results are shown in Table 2.

TABLE 2

| ANALOG | Number of N-linked Carbohydrate Chains | In Vitro Activity ** |
|---|---|---|
| rHuEpo | 3 | +++ |
| N49 | 4 | +++ |
| N50 | 4 | +++ |
| N51 | 5* | +++ |
| N52 | 3-4 | +++ |
| N53 | 6 | ++ |
| N54 | 4 | NT |
| N55 | 4 | +++ |
| N56 | 4 | +++ |
| N57 | 3-4 | +++ |
| N58 | 4 | +++ |
| N59 | 5 | ++ |
| N60 | 4-5 | +++ |
| N61 | 6-7 | NT |

*contains 1-2 O-linked chains
** In vitro activity is relative to rHuEpo activity
+++ activity equivalent to rHuEpo
++ activity is 25-75% of rHuEpo
NT Not Tested Epo analogs N62-N69 were made by overlap PCR (polymerase chain reaction) methods. The basic procedure included two successive steps. In the first step, two reactions (PCR1 and PCR2) were performed on Epo or Epo analog template DNA using a total of four oligonucleotides: a 5' (forward) primer, a reverse mutagenic primer, a forward mutagenic primer complementary to the reverse mutagenic primer and a 3' (reverse) primer. The mutagenic primers contained the desired nucleotide changes as well as 6-14 exact match nucleotides on each side of these changes. PCR1 used the 5' (forward) primer and the reverse mutagenic primer. PCR2 used the 3' (reverse) primer and the forward mutagenic primer. The amplified DNA fragments were separated by agarose gel electrophoresis and DNA fragments of the correct size were excised and eluted from the gel. The DNA fragments from PCR1 and PCR2 were combined together and a third PCR reaction was performed using only the 5' forward and 3' reverse primers. For some analogs, three PCR reactions were required to generate the desired sequence. These were carried out as above, with a second pair of mutagenic primers being used to generate the third product. Again, the amplified DNA fragments were gel purified and combined in a final reaction containing only the 5' forward and 3' reverse primers.

In each case, a full length DNA segment containing the desired mutations was amplified.

N62 added two glycosylation sites (N30 T32 N55 T57) to native sequence HuEpo by using pDSRα2 Epo N4 (N30 T32) as PCR template. N63 added three glycosylation sites (N30 T32 N55 T57 V87 N88 T90) to native sequence HuEpo by using pDSRα2 Epo N4 (N30 T32) and pDSRα2 Epo N47 (N30 T32 N55 T57) as PCR templates. N64 added three glycosylation sites (N30 T32 N55 T57 N114 T116) to native sequence HuEpo by using pDSRα2 Epo N4 (N30 T32) and pDSRα2 Epo N60 as PCR templates. N65 added three glycosylation sites (N30 T32 V87 N88 T90 N114 T116) to native sequence HuEpo by using pDSRα2 Epo N4 (N30 T32) and pDSRα2 Epo N60 as PCR templates. N66 added four glycosylation sites (N30 T32 N55 T57 V87 N88 T90 N114 T116) to native sequence HuEpo by using pDSRα2 Epo N4 (N30 T32) and pDSRα2 Epo N60 as PCR templates. N67 added an O-linked glycosylation site (P124 T125 T 126) to N64 Epo. N68 added an O-linked glycosylation site (P124 T125 T 126) to N65 Epo. N69 added an O-linked glycosylation site (P124 T125 T 126) to N66 Epo.

For each analog, the same outside primers were used. The 3' (reverse) primer contained sequences that introduced a stop codon followed by a Sal I restriction site:

```
                                          (SEQ ID NO: 11)
AGGTGGACAGTCGACATTATCTGTCCCCTGTC.
```

The 5' forward reaction primer:

```
AACAAGCTTCTAGACCACCATGGGGGTG        (SEQ ID NO: 12)
``` had a Hind III restriction site followed by a Kozak sequence upstream of the Epo initiator codon (ATG). Mutagenic primers were as follows:

```
N30 T32 mutagenic forward primer
                                          (SEQ ID NO: 13)
ACG ACG GGC TGT AAT GAA ACG TGC AGC TTG N30 T32 mutagenic reverse primer
                                          (SEQ ID NO: 14)
CAA GCT GCA CGT TTC ATT ACA GCC CGT CGT G N55 T57 mutagenic forward primer
                                          (SEQ ID NO: 15)
GCC TGG AAG AGG ATG AAT GTC ACGCAG CAG GCC GTA
GAA N55 T57 mutagenic reverse primer
                                          (SEQ ID NO: 16)
TTC TAC GGC CTG CTG CGT GAC ATTCAT CCT CTT CCA
GGC A V87 N88 T90 mutagenic forward primer
                                          (SEQ ID NO: 17)
TCT TCC CAG GTG AAT GAG ACC CTG CAG CTG V87 N88 T90 mutagenic reverse primer
                                          (SEQ ID NO: 18)
CAG CTG CAG GGT CTC ATT CAC CTG GGA AGA GTT G P124 T125 T126 mutagenic forward primer
                                          (SEQ ID NO: 19)
CCA GAT CCG ACC ACA GCT GCT CCA P124 T125 T126 mutagenic reverse primer
                                          (SEQ ID NO: 20)
TGG AGC AGC TGT GGT CGG ATC TGG A
```

The N114 T116 changes were introduced using a template containing the appropriate mutations, so no mutagenic primers were required to generate this site.

The typical PCR1 reaction mix contained: 2.5 μl each of forward and mutagenic reverse primers (10 pmol/μl), 1 μl template (25 ng), 10 μl of 10× Taq Extend buffer (Stratagene), 2 μl dNTP stock (10 mM each of dATP, dTTP, dCTP, dGTP), 0.5 μl Taq polymerase (BMB), and 0.5 μl Taq Extend (Stratagene). H$_2$O was added to bring the final volume to 100 μl. Typical reaction conditions were: 1 cycle of 94° C., 5 min./55° C., 1 min./68° C., 1 min. followed by 25 cycles of 94° C., 1 min./55° C., 1 min./68° C., 1 min. The typical PCR2 reaction was identical to that described for PCR 1, except that the reverse and mutagenic forward primers were used. Where a third initial reaction was required, the reaction contained mutagenic forward and mutagenic reverse primers. The amplified fragments were separated by agarose gel electrophoresis and the correct sized DNA fragment was purified using a Gel Extraction kit and procedures supplied by the manufacturer (Qiagen). Complementary fragments were then combined in a third PCR reaction using only the outside forward and reverse primers. The amplified fragments were separated by agarose gel electrophoresis and purified from the gel as described above. The purified DNA was digested with Hind III and Sal I, then it was again gel purified. The fragment was then ligated into Hind III and Sal I cut pDSRα19 vector. Ligated DNA transformed by electroporation into *E. coli*. Epo hyperglycosylated analogs were initially screened by colony PCR to identify clones containing the correctly sized DNA insert. Plasmid DNA from selected clones was then prepared and the insert was sequenced to confirm the presence of the desired mutations and to ensure that no additional amino acid changes were introduced.

TABLE 3

ERYTHROPOIETIN ANALOGS HAVING SITES
FOR N-LINKED CARBOHYDRATE CHAINS

| Analog | Amino Acid Substitution | Sequence Changes |
|---|---|---|
| N62 | Ala, His, Glu, Gly→ Asn30, Thr32, Asn55 Thr57 | GCT, CAC, GAG, GGG→ AAT, ACG, AAT, ACT |
| N63 | A, H, E, G, P, W, P→ N30, T32, N55, T57, V87, N88, T90 | GCT, CAC, GAG, GGG, CCG, TGG, CCC→ AAT, ACG, AAT,, ACT GTG, AAT, ACC |
| N64 | A, H, E, G, A, K→ N30, T32, N55, T57, N114 T116 | GCT, CAC, GAG, GGG, GCC, AAG→ AAT, ACG, AAT, ACT, AAC, ACG |

TABLE 3-continued

ERYTHROPOIETIN ANALOGS HAVING SITES
FOR N-LINKED CARBOHYDRATE CHAINS

| Analog | Amino Acid Substitution | Sequence Changes |
|---|---|---|
| N65 | A, H, P, W, P, A, K→<br>N30, T32, V87, N88, T90, N114, T116 | GCT, CAC, CCG, TGG, CCC, GCC,<br>AAG→ AAT, ACG, GTG, AAT, ACC,<br>AAC, ACG |
| N66 | A, H, E, G, P, W, P, A, K→<br>N30, T32, N55, T57, V87, N88, T90,<br>N114, T116 | GCT, CAC, GAG, GGG, CCG, TGG,<br>CCC, GCC, AAG→<br>AAT, ACG, AAT,, ACT GTG, AAT,<br>ACC, AAC, ACG |
| N67 | A, H, E, G, P, W, P, A, A, S→<br>N30, T32, N55, T57, V87, N88, T90,<br>P124, T125, T126 | GCT, CAC, GAG, GGG, CCG, TGG,<br>CCC, GCG, GCC, TCA→<br>AAT, ACG, AAT, ACT GTG, AAT,<br>ACC, CCG ACC ACA |
| N68 | A, H, E, G, A, K, A, A, S→<br>N30, T32, N55, T57, N114 T116,<br>P124,<br>T125, T126 | GCT, CAC, GAG, GGG, GCC, AAG,<br>GCG, GCC, TCA→<br>AAT, ACG, AAT, ACT, AAC, ACG,<br>CCG, ACC, ACA |
| N69 | A, H, E, G, P, W, P, A, K, A, A,<br>S→<br>N30, T32, N55, T57, V87, N88, T90,<br>N114, T116, P124, T125, T126 | GCT, CAC, GAG, GGG, CCG, TGG,<br>CCC, GCC, AAG, GCG, GCC, TCA→<br>AAT, ACG, AAT, ACT GTG, AAT, ACC,<br>AAC, ACG, CCG, ACC, ACA |
| N70 | Ala, His, Pro, Trp, Pro→<br>N30, T32, V87, N88, T90,<br>IgG1 fusion | GCT, CAC, CCG, TGG, CCC→AAT,<br>ACG,GTG, AAT, ACC |

Construction of cDNA Encoding Hyperglycosylated Epo Analog Fusion Polypeptide

Epo analog N70 was also made by overlap PCR. Plasmid DSRα2 containing the cDNA sequence encoding analog N47 (N30 T32 V87 N88 T90) and plasmid pAMG21 (ATCC accession no. 98113) containing cDNA encoding an Fc region were used as templates for the polymerase chain reactions. The Fc portion of human immunoglobulin IgG1 heavy chain from residue 104 of the hinge domain(Asp-104) to the carboxyl terminus (Ellison et al., supra, see also FIG. 10 (SEQ ID NO: 25) starting at aspartic acid residue at position 6), was generated by PCR amplification of a human spleen cDNA library (Clontech). Overlapping PCR products were generated in two reactions using the following oligonucleotide primers 5' forward reaction primer 2343-85 (Epo specific):

(SEQ ID NO: 21)
AAC AAG CTT CTA GAC CAC CAT GGG GGT G

3' reverse reaction primer 2343-87 (homology to both Epo and Fc):

(SEQ ID NO: 22)
AGG TGG ACA TGT GTG AGT TTT GTC TCT GTC CCC TCT

CCT GCA GGC CTC C

5' forward reaction primer 2343-86 (homology to both Epo and Fc):

(SEQ ID NO: 23)
GAG GCC TGC AGG ACA GGG GAC AGA GAC AAA ACT CAC

ACA TGT CCA CCT

3' reverse reaction primer 2343-88 (specific to Fc):

(SEQ ID NO: 24)
TGG ACA GTC GAC ATT ATT TAC CCG GAG ACA GGG AGA

GGC TCT TCT GC

PCR1 contained 2.5 μl each of forward (2343-85) and reverse (2343-87) primers (10 pmol/μl), while PCR2 contained 2.5 μl each of forward (2343-86) and reverse (2343-88) primers (10 pmol/μl). Conditions were as described above. The resulting amplified products contained a region of overlap (48 nucleotides) encoding the last 8 amino acids of Epo and the first 8 amino acids of Fc. The complementary fragments were gel purified and combined in a third PCR reaction using only the outside forward and reverse primers. The amplified fragment was separated by agarose gel electrophoresis and purified from the gel as described above. The purified DNA was digested with Hind III and Sal I, then it was again gel purified. The fragment was then ligated into Hind III and Sal I cut pDSRα19 vector. Ligated DNA transformed by electroporation into *E. coli*. Transformants were initially screened by colony PCR to identify clones containing the correctly sized DNA insert. Plasmid DNA from selected clones was then prepared and the insert was sequenced to confirm the sequence of the fusion protein and to ensure that no additional amino acid changes were introduced.

Analysis of Carbohydrate Addition

The constructs for the hyperglycosylated Epo analogs N62 to N69 and fusion protein (analog N70) were inserted into the expression vector pDSRα19 and transfected into CHO cells. Supernatants from the transfected CHO cells are analyzed by western blot to determine whether the expressed and secreted Epo analogs contained additional carbohydrate using procedures described above for analogs N49 to N62.

In Vitro Bioassays

In vitro assays for analogs N62 to N70 expressed in CHO transfected cells are performed as described above for analogs N49 to N61.

EXAMPLE 2

Preparation of Recombinant Human Erythropoietin and Hyperglycosylated Erythropoietin Analogs Recombinant human erythropoietin (rHuEpo) used for the experiments described herein was expressed by Chinese hamster ovary (CHO) cells transfected with a recombinant plasmid carrying the human erythropoietin gene. The recombinant product was recovered from the conditioned medium and purified essentially as described by Lai et al. supra. The resulting rHuEpo preparation has predominantly isoforms of 9 to 14 sialic acids as determined by isoelectric focusing.

Recombinant hyperglycosylated erythropoietin analogs were expressed in CHO cells transfected with a recombinant plasmid carrying the Epo analog gene as described WO91/05867 and WO94/09257 hereby incorporated by reference. The hyperglycosylated analogs were purified from culture supernatants as described below.

Concentration and Diafiltration of Conditioned Media

Conditioned medium (serum free) from three successive harvests (5-8 days each) of the transfected CHO cell line was collected, filtered through a 0.45 µm filter, concentrated about thirty fold, and diafiltered into 10 mM Tris, 20 µM $CuSO_4$, pH 7.0 using a tangential-flow ultrafiltration system (Millipore) with a 10,000 molecular weight cutoff membrane. The dial-filtered media (DFM) was filtered (0.45 µm) a second time and stored at −20° C. until used for purification.

Purification

All procedures were carried out at 2 to 8° C.

Anion—Exchange Chromatography (1Q)

The clarified DFM was applied to a Q-Sepharose Fast Flow column (Pharmacia, 6 cm×18 cm) equilibrated in 10 mM bis Tris propane (BTP), pH 7.0 and washed with two column volumes of 10 mM BTP to elute all non-binding species. The following gradients were run depending upon whether the hyperglycosylated analog had four, five or six N-linked carbohydrate chains. All buffers used at this stage contain 1 mM glycine, 20 µM $CuSO_4$, 6 M urea, 5 µg/mL leupeptin and 1 µg/mL pepstatin. For analogs with four N-linked carbohydrate chains, the gradient was 10 mM acetic acid, 0.1 mM NaCl to 500 mM acetic acid, 5 mM NaCl over 49 column volumes with a two column volume hold at high salt conditions. For analogs with five N-linked carbohydrate chains, the gradient was 0.7 M acetic acid, 7 mM NaCl to 1.0 M acetic acid, 12 mM NaCl over 30 column volumes with a two column volume hold at high salt conditions. For analogs with six N-linked carbohydrate chains, the gradient was 1.0 M acetic acid, 10 mM NaCl to 1.5 M acetic acid, 20 mM NaCl over 50 column volumes with a two column volume hold at high salt conditions. Following the gradient, the column was washed with two column volumes of 10 mM BTP, pH 7.0 and the high isoform fraction was eluted with 0.6 M NaCl, 100 mM BTP, pH 7.0.

Reversed Phase Chromatography (C4)

The high salt strip from the Q-Sepharose column (1Q) was applied to a Vydac C4 reversed phase column (30µ particles, 4 cm×18 cm) equilibrated in 20% ethanol, 10 mM BTP, pH 7.0 and eluted from the column with a thirty column volume gradient to 94% ethanol buffered in 10 mM BTP, pH 7.0. The pooled product peak, eluting in approximately 60% ethanol, was diluted with four volumes of 10 mM BTP, pH 7.0 to minimize possibility of aggregation in the presence of ethanol.

Anion—Exchange Chromatography (2Q)

The diluted eluate from the reversed phase column was applied to a second Q-Sepharose Fast Flow (Pharmacia, 3 cm×9 cm) column equilibrated with 10 mM BTP, pH 7.0. The column was washed with equilibration buffer, and the hyperglycosylated Epo analog was eluted with 0.6 M sodium chloride, 20 mM sodium citrate, pH 6.0.

The purified protein was exchanged into 20 mM $NaPO_4$, pH 6.0, 140 mM NaCl via centricon (10,000 molecular weight cutoff), followed by passage through a 0.2 µm filter and storage at 2-8° C.

EXAMPLE 3

In Vivo Bioactivity of rHuEpo and rHuEpo Analogs Containing Four, Five and Six N-Linked Carbohydrate Chains The in vivo activity of Epo analogs containing four, five and six N-linked carbohydrate chains was compared with that of rHuEpo in the exhypoxic polycythemic mouse bioassay. This assay quantifies the incorporation of $^{59}Fe$ into newly synthesized red blood cells as a measure of the increase in erythropoiesis in mice in response to an exogenously-administered test sample. The assay, performed as described below, is a modification of the method of Cotes and Bangham (Nature 191, 1065 (1961)).

In this assay, female BDF mice are first preconditioned by exposure to low oxygen conditions in a hypobaric chamber (0.4-0.5 atm.) for approximately 18 hours a day for 14 days. To compensate for the low oxygen conditions the mice respond by stimulating erythropoiesis to increase the number of red blood cells and thereby the relative oxygen-carrying capacity. After completion of the final hypobaric exposure, the mice are allowed to remain at ambient pressure for approximately 72 hours prior to the administration of test samples by intraperitoneal injection. At ambient pressure the mice are relatively polycythemic and respond by decreasing endogenous erythropoietin production and the rate of erythropoiesis. Five days after sample administration, 0.2-0.3 µCi of $^{59}FeCl_3$ in 0.2 mL is injected intravenously into the tail vein. Forty-eight hours later, the animals are sacrificed and the increase in erythropoiesis produced by the test samples is determined by measuring the amount of $^{59}Fe$ incorporated in a 0.5 mL sample of whole blood.

An example of the results obtained when rHuEpo and five different Epo analogs, containing four, five or six N-linked carbohydrate chains were tested in this assay is shown in FIG. 3. Each sample was assayed at six or seven different dilutions within an appropriate concentration range. All samples were diluted in phosphate-buffered saline containing 0.5% bovine serum albumin, and 0.4 mL of each dilution was administered to five preconditioned mice. Forty-eight hours after the administration of $^{59}Fe$, the amount incorporated in 0.5 mL of blood was measured by gamma counting. The results for each of the samples are plotted as the percent $^{59}Fe$ incorporated versus the log of the administered dose.

As shown in FIG. 3, all five of the hyperglycosylated Epo analogs tested in this assay were more potent than rHuEpo. In addition, the potency of each analog was directly dependent on the number of N-linked carbohydrate chains, with those analogs having an increased number of carbohydrate chains having the greater activity. Thus, analog N53, which contains six N-linked carbohydrate chains, was the most potent analog. Analog N47, which contains five N-linked carbohydrate chains, was in turn, more potent than those analogs containing four N-linked chains. The potencies of the three analogs containing four N-linked carbohydrate chains (N4, N18 and N50) were approximately equal to each other and greater than that of rHuEpo.

In this experiment, the doses of rHuEpo and analogs containing four, five or six N-linked carbohydrate chains required to produce 40% $^{59}$Fe incorporation were 10,700 ng, 640 ng, 140 ng and 38 ng, respectively. Based on the amount of material required to produce this level of erythropoiesis, Epo analogs containing four, five, or six N-linked carbohydrate chains are 17-fold, 77-fold and 280-fold more potent than rHuEpo.

EXAMPLE 4

IV Pharmacokinetics of rHuEpo and Epo Analog N47 in Rats and Beagle Dogs

Two separate studies in rats and dogs were performed to compare the pharmacokinetic parameters of Epo N47 analog and rHuEpo.

In the rat studies, 1 µCi (~0.1 µg of peptide/kg) of either $^{125}$I-Epo N47 analog, or $^{125}$I-recombinant human erythropoietin (Amersham) was injected intravenously into a surgically implanted carotid cannula in normal male Sprague-Dawley rats weighing between 314-363 g. At various time points after administration, 0.3 mL of blood was collected and serum was prepared by centrifugation. The level of 125I-rHuEpo or $^{125}$I Epo N47 analog in 0.1 mL of each serum sample was then determined following an overnight 4° C. incubation with 90% ethanol. The ethanol-precipitated protein in each serum sample was collected by centrifugation and the radioactivity was counted in a gamma counter. The resulting serum concentration vs time pharmacokinetic curves are shown in FIG. 4. Each point represents a group mean of five rats in the N47 analog group and six rats in the rHuEpo group. The pharmacokinetic parameters were determined for each rat using PCNONLIN 4.0 nonlinear regression analysis (Statistical Consultants, 1992) and the results for each group were averaged. The results are shown in Table 3.

TABLE 3

Comparison of IV Pharmacokinetic Parameters of N47 and r-HuEpo in Rats

| Sample Test | Half-life | | $V_d$ (mL/kg) | Serum Clearance (mL/kg-hr) |
|---|---|---|---|---|
| | α (hours) | β (hours) | | |
| N47 (n = 5 rats) | 0.57 ± 0.49 | 6.9 ± 0.3 | 33 ± 5 | 4.8 ± 1.2 |
| r-HuEpo (n = 6 rats) | 0.18 ± 0.03 | 2.5 ± 0.2 | 36 ± 6 | 17.7 ± 3.4 | a The results are presented as the group average ± SD for five rats in the N47 group and six rats in the r-HuEpo group.

In the dog studies, normal Beagle dogs weighing between 7.8-9.5 kg received an intravenous bolus injection of ~29 µCi of either $^{125}$I-rHuEpo or $^{125}$I-N47 (~0.1 µg peptide/kg) into the cephalic vein. At various time points through 24 hours post-administration, approximately 1 to 2 mL of blood was collected and serum prepared. The concentration of $^{125}$I-rHuEPo and $^{125}$I-N47 in 0.1 mL serum was determined and pharmacokinetic parameters were calculated as described above. The serum concentration vs time pharmacokinetic curves for the dog studies are shown in FIG. 5. The time points are the group means of two animals in each group. The pharmacokinetic parameters are summarized in Table 4.

TABLE 4

Comparison of IV Pharmacokinetic Parameters of N47 and r-HuEpo in Dogs

| Sample Test | Half-life | | $V_d$ (mL/kg) | Serum Clearance (mL/kg-hr) |
|---|---|---|---|---|
| | α (hours) | β (hours) | | |
| N47 | 0.34 | 25.0 | 55.9 | 2.4 |
| r-HuEpo | 0.40 | 7.2 | 60.8 | 8.4 | a The results presented are the average parameters for the two dogs in each group.

In both the rat and dog studies, rHuEpo and Epo N47 analog exhibited a biphasic serum clearance. Clearance in rats was about 3.7-fold faster for rHuEpo than for Epo N47 analog and the β-half-life was about 2.8-fold longer for Epo N47 analog than for rHuEpo. The pharmacokinetic parameters in the dog studies were generally consistent with those observed in rat. In dogs, the clearance of rHuEpo was 3.5-fold faster than for Epo N47 analog and the β-half-life was 3.5-fold longer for Epo N47 analog compared with that for rHuEpo.

EXAMPLE 5

Dose Response of Hematocrit After Administration of rHuEpo and Epo analog N47

Hematocrit Dose Response Studies at Three Times Per Week (TIW)

The in vivo biological effects of rHuEpo and Epo analog N47 in normal mice were compared after administering a range of doses by either intraperitoneal or intravenous injection three times per week for up to six weeks. Hematocrit determinations were performed twice weekly by retro-orbital bleed.

Normal CD1 mice weighing approximately 30 g (10-13 mice per group) were injected intraperitonally three times per week for a total of six weeks with either rHuEpo (over the dose range of 0.625-10 µg peptide/kg/dose), Epo N47 analog (over the dose range of 0.156-1.25 µg peptide/kg/dose) or vehicle control. The vehicle control and diluent for the various rHuEpo and Epo N47 analog dosing preparations was phosphate-buffered saline (PBS), containing 0.025% mouse serum albumin. The hematocrits of all mice were determined at baseline and twice weekly thereafter by retro-orbital bleeds. At the conclusion of the experiment, serum from all animals was collected and assayed for antibodies to the injected product by a solution radioimmunoprecipitation assay. Hematocrit data from animals judged to be negative for neutralizing antibodies were used for subsequent analysis.

As shown in FIG. 6 both rHuEpo and Epo N47 analog produce a dose-dependent increase in hematocrit in the six week study, although N47 analog promotes a greater increase in hematocrit compared to rHuEpo at a given concentration. In this experiment the Epo N47 analog is about 3 to 4-fold more potent when dosed three times per week by intraperitoneal injection.

Dose response studies of rHuEpo and analog N47 were carried out by intravenous injection three times per week using procedures similar to those for intraperitoneal injection. The results obtained were similar to those for intraperitoneal administration and, in particular, the studies further confirmed that Epo N47 analog had a greater potency than rHuEpo when administered three times per week.

To better compare and quantify the biological activity of rHuEpo and Epo N47 analog in raising the hematocrit of normal mice, results of experiments were also analyzed by relative potency plots. For each experiment, the activity of rHuEpo or N47 analog at each dose was determined by summing the increase in hematocrit over the first 38 days of the study by trapezoidal summation to obtain the area under the curve (AUC). This was then plotted versus the log dose in μg peptide/kg/week. Potency difference between compounds administered by the same or different routes of administration or dosing frequencies can be determined by measuring the distance between the relevant log-dose response lines. FIG. 7 summarizes the relative potency data for all experiments performed comparing the activity of rHuEpo and Epo N47 analog administered by two different routes (intraperitoneal and intravenous) and at two different dosing schedules.

As shown in FIG. 7 when administered three times per week, Epo N47 analog has the same potency when injected by either the intravenous or intraperitoneal route and was 3.6-fold more potent than rHuEpo injected intraperitoneally three times weekly.

Hematocrit Dose Response Studies at One Time Per Week (OW)

Comparisons of rHuEpo and Epo analog N47 at increasing hematocrit in normal mice were undertaken with once weekly dosing by either the intraperitoneal or intravenous routes of administration for six weeks.

Normal CD1 mice weighing approximately 30 g (8-10 mice per group) were injected intravenously once weekly for a total of six weeks with varying concentrations of either rHuEpo or Epo N47 analog prepared in PBS containing 0.025% mouse serum albumin, or with vehicle control (PBS with 0.025% mouse serum albumin). The analog dose varied from 6.25-25 μg of peptide/kg/dose and the dose of rHuEpo varied from 25-200 μg/kg/dose. The hematocrits of all mice were determined at baseline and twice weekly thereafter by retro-orbital bleeds. At the conclusion of the experiment, serum from all animals was collected and assayed for antibodies to the injected product by a solution radioimmunoprecipitation. Data from animals judged to be negative for neutralizing antibodies were used for subsequent analysis.

As shown in FIG. 8, whereas both rHuEpo and analog N47 can increase the hematocrit of normal mice when dosed once weekly, the dose of rHuEpo required to produce a response was significantly greater than that for analog N47. For instance, in this experiment 25 μg peptide/kg/week of N47 increased the hematocrit of mice by 41.2 points in six weeks, whereas the same dose of rHuEpo produced only a 12.5 point hematocrit rise.

Dose response studies of rHuEpo and analog N47 were performed by intraperitoneal injection once weekly using procedures similar to those described above. The results obtained were consistent with the results for intravenous administration and further confirmed the greater potency of analog N47 compared with rHuEpo when administered one time per week.

To quantify the activity difference between rHuEpo and N47 analog when each is dosed once weekly, relative potency plots were generated from all relevant experiments as described above. As shown in FIG. 7, when administered one time per week, analog N47 has the same potency when injected by the intravenous and intraperitoneal route. Analog N47 is approximately 14-fold more potent than rHuEpo when each is administered once weekly.

In addition, the log-dose response plots in FIG. 6 also illustrate the following: (1) A given dose of analog N47 administered once weekly (QW) is approximately as effective as the same total weekly dose of rHuEpo given as three divided doses (TIW); (2) A given dose of rHuEpo administered once weekly (QW) is only approximately 2% as effective as the same total weekly dose of analog N47 given as three divided doses (TIW); (3) Analog N47 is approximately 4-fold more potent in mice when administered TIW compared to QW.

Hematocrit Dose Response Studies at Every Other Week (EOW)

Experiments were also undertaken to assess the ability of analog N47 to increase the hematocrit of mice when injected once every other week. Normal CD-1 mice (10 mice per group) were injected intravenously either once weekly or once every other week for a total of approximately six weeks with varying concentrations of Epo N47 analog prepared in PBS containing 0.025% mouse serum albumin. Analog N47 was administered at either 200, 100 or 25 μg/kg/dose every other week or at 12.5 μg/kg/dose once weekly. The hematocrits of all mice were determined at baseline and twice weekly thereafter by retroorbital bleeds.

As shown in FIG. 9, analog N47 can increase the hematocrit of normal mice in a dose-dependent fashion even when administered bi-monthly. As expected when dosed less frequently, a greater amount of N47 analog is required to increase the hematocrit. A dose of 200 μg/kg of N47 analog administered every other week increased the hematocrit to approximately the same extent in six weeks as did 12.5 μg/kg when dosed weekly.

EXAMPLE 6

IV Pharmacokinetics of Epo N47 Analog and rHuEpo in Continuous Ambulatory Peritoneal Dialysis (CAPD) Patients In view of the marked increase in serum half-life of Epo N47 analog compared to rHuEpo in rat and beagle dog, it was of interest to determine whether an increase could also be observed in humans.

A double-blind, randomized cross-over design study of eleven stable CAPD patients (7 males, 4 females, aged 27-75 years) was undertaken. One patient group received 100 U/kg of rHuEpo (equivalent to 0.5 μg of peptide/kg) while a second group of patients received 0.5 μg peptide/kg of Epo N47 analog, both administered as a single bolus injection intravenous. Venous blood samples (3 mL) were drawn via an indwelling cannula and were taken pre-dose and at 5, 10, 15, 30 minutes and 1, 2, 5, 8, 12, 16, 24, 30, 36, 48, 60, 72 and 96 hours after the intravenous bolus. After a 28 day washout period, the first patient group received a single intravenous dose of Epo analog N47 while the second group received a single intravenous dose of rHuEpo. Blood samples were taken as in the first cycle of treatment. Levels of rHuEpo and Epo N47 analog were determined in serum by ELISA after subtraction of baseline endogenous Epo levels. The pharmacokinetic parameters (mean±SE) estimated after adjustment for cross-over design effects are shown in Table 5. The serum concentration AUC was calculated using the linear trapezoidal summation. $t\frac{1}{2}_z$ is defined as: $\log(2)/K_z$, where $K_z$ is calculated as the slope of the terminal portion of the ln (serum concentration) time curve. The clearance (Cl) is defined as: dose/AUC. The volume of distribution ($V_d$) is defined as: Cl/K.

TABLE 5

| Dose Group | AUC (ng · h/mL) | $t_{1/2z}$ (h) | Cl (mL/h/kg) | Vd (mL/kg) |
|---|---|---|---|---|
| N47 | 291.0 ± 7.6 | 25.3 ± 2.2 | 1.6 ± 0.3 | 52.4 ± 2.0 |
| rHuEpo | 131.9 ± 8.3 | 8.5 ± 2.4 | 4.0 ± 0.3 | 48.7 ± 2.1 |

The mean serum half-life for Epo N47 analog (25.3 hr) was three times longer than for rHuEpo (8.5 hr) and the clearance was 2.5-fold faster for rHuEpo than for analog N47.

EXAMPLE 7

A Phase II Dose Finding and Dose Scheduling Study of Epo N47 Analog

Multicenter, randomized, sequential dose-escalation studies are initiated to investigate the optimum dose and dose schedule for analog N47 when administered by subcutaneous or intravenous injection in patients with CRF receiving dialysis.

The dosing schedule is as follows:

Once per week dosing: 0.075, 0.225, 0.45, 0.75, 1.5 and 4.5 µg of peptide/kg/dose.

Three times per week dosing: 0.025, 0.075, 0.15, 0.25, 0.5 and 1.5 µJg of peptide/kg/dose.

The studies are carried out in two parts: the first part is a dose-escalation study designed to evaluate the dose of analog N47 given either one or three times per week which increases hemoglobin at an optimum rate over four weeks (greater than or equal to 1 g/dL but less than 3 g/dL). The second part of each study is designed to determine the doses required (when administered once or three times per week by either the intravenous or subcutaneous routes of administration) to maintain the hematocrit at the therapeutic target.

Preliminary results indicate that once weekly dosing with analog N47 can be used to both increase and maintain the hematocrit of anemic CRF patients. Initial results suggest that the preferred doses to initiate therapy on a three times a week dosing schedule are 0.15 and 0.25 µg/peptide/kg/dose, and on a one time per week dosing schedule are 0.45 and 0.75 µg/peptide/kg/dose for both routes of administration.

While the invention has been described in what is considered to be its preferred embodiments, it is not to be limited to the disclosed embodiments, but on the contrary, is intended to cover various modifications and equivalents included within the spirit and scope of the appended claims, which scope is to be accorded the broadest interpretation so as to encompass all such modifications and equivalents.

What is claimed is:

1. A nucleic acid molecule encoding an analog of human erythropoietin comprising the amino acid sequence of human erythropoietin from residues 1-165 as shown in SEQ ID NO:1 except for one or more amino acid changes which provide for one or more additional glycosylation site(s) as compared to human erythropoietin, wherein one additional site is introduced at position 52, 53, 55, 86 or 114 and an N-linked carbohydrate chain is attached at said one additional site.

2. The nucleic acid molecule of claim 1 wherein the analog comprises three, four, or more than four additional glycosylation sites wherein a carbohydrate chain is attached at each said additional site.

3. The nucleic acid molecule of claim 1 wherein additional glycosylation sites are introduced at positions 30 and 55 and N-linked carbohydrate chains are attached at the additional sites.

4. The nucleic acid molecule of claim 1 wherein additional glycosylation sites are introduced at positions 30 and 114 and N-linked carbohydrate chains are attached at the additional sites.

5. The nucleic acid molecule of claim 1 wherein additional glycosylation sites are introduced at positions 30, 55 and 88 and N-linked carbohydrate chains are attached at the additional sites.

6. The nucleic acid molecule of claim 1 wherein additional glycosylation sites are introduced at positions 30, 55 and 114 and N-linked carbohydrate chains are attached at the additional sites.

7. The nucleic acid molecule of claim 1 wherein additional glycosylation sites are introduced at positions 30, 88 and 114 and N-linked carbohydrate chains are attached at the additional sites.

8. The nucleic acid molecule of claim 1 wherein additional glycosylation sites are introduced at positions 30, 55, 88 and 114 and an N-linked carbohydrate chain is attached at the additional sites.

9. The nucleic acid molecule of claim 1 further comprising an additional glycosylation site at position 125 and wherein an O-linked carbohydrate chain is attached at the additional site.

10. A nucleic acid molecule encoding an analog of human erythropoietin comprising the amino acid sequence from residues 1-165 as shown in SEQ ID N0:1 except for Asn at position 30, Thr at position 32, Asn at position 55, Thr at position 57, Val at position 87, Asn at position 88, Thr at position 90, Asn at position 114, Thr at position 116, and any one or more of Pro at position 124, Thr at position 125 and Thr at position 126.

11. A nucleic acid molecule encoding an analog of human erythropoietin comprising the amino acid sequence from residues 1-165 as shown in SEQ ID NO:1 except for the amino acid changes selected from the group consisting of:

$Asn^{52}$ $Thr^{54}$ Epo;
$Asn^{53}$ $Thr^{55}$ Epo;
$Asn^{114}$ $Thr^{116}$ Epo;
$Asn^{30}$ $Thr^{32}$ $Asn^{53}$ $Thr^{55}$ $Val^{87}$ $Asn^{88}$ $Thr^{90}$ Epo;
$Asn^{55}$ $Thr^{57}$ Epo;
$Asn^{86}$ $Val^{87}$ $Thr^{88}$ Epo;
$Asn^{30}$ $Thr^{32}$ $Asn^{53}$ $Thr^{55}$ Epo;
$Asn^{30}$ $Thr^{32}$ $Asn^{114}$ $Thr^{116}$ Epo;
$Asn^{30}$ $Thr^{32}$ $Asn^{53}$ $Thr^{55}$ $Val^{87}$ $Asn^{88}$ $Thr^{90}$ $Asn^{114}$ $Thr^{116}$ Epo;
$Asn^{30}$ $Thr^{32}$ $Asn^{55}$ $Thr^{57}$ Epo;
$Asn^{30}$ $Thr^{32}$ $Asn^{55}$ $Thr^{57}$ $Val^{87}$ $Asn^{88}$ $Thr^{90}$ Epo;
$Asn^{30}$ $Thr^{32}$ $Asn^{55}$ $Thr^{57}$ $Asn^{114}$ $Thr^{116}$ Epo;
$Asn^{30}$ $Thr^{32}$ $Val^{87}$ $Asn^{88}$ $Thr^{90}$ $Asn^{114}$ $Thr^{116}$ Epo;
$Asn^{30}$ $Thr^{32}$ $Asn^{55}$ $Thr^{57}$ $Val^{87}$ $Asn^{88}$ $Thr^{90}$ $Asn^{114}$ $Thr^{116}$ Epo;
$Asn^{30}$ $Thr^{32}$ $Asn^{55}$ $Thr^{57}$ $Val^{87}$ $Asn^{88}$ $Thr^{90}$ $Pro^{124}$ $Thr^{125}$ $Thr^{126}$ Epo;
$Asn^{30}$ $Thr^{32}$ $Asn^{55}$ $Thr^{57}$ $Asn^{114}$ $Thr^{116}$ $Pro^{124}$ $Thr^{125}$ $Thr^{126}$ Epo; and
$Asn^{30}$ $Thr^{32}$ $Asn^{55}$ $Thr^{57}$ $Val^{87}$ $Asn^{88}$ $Thr^{90}$ $Asn^{114}$ $Thr^{116}$ $Pro^{124}$ $Thr^{125}$ $Thr^{126}$ Epo.

12. An expression vector comprising the nucleic acid molecule of claim 1, 10 or 11.

13. A eucaryotic host cell in culture comprising the nucleic acid molecule of claim 1, 10 or 11.

14. A eucaryotic host cell in culture comprising the expression vector of claim 12.

15. The host cell of claim 13 or 14 which is a mammalian host cell.

16. The host cell of claim 13 or 14 which is a human host cell.

17. The host cell of claim 14 which is selected from the group consisting of COS-7, BHK, CHO, 293, HeLa, L-929 and 3T3 cells.

18. A method of producing an analog of human erythropoietin comprising culturing a host cell of claim 13 or 14 under conditions that permit expression of the analog and recovering the analog.

* * * * *

SEQUENCE LISTING

```
<160> NUMBER OF SEQ ID NOS: 27

<210> SEQ ID NO 1
<211> LENGTH: 193
<212> TYPE: PRT
<213> ORGANISM: Homo sapiens
<220> FEATURE:
<221> NAME/KEY: sig_peptide
<222> LOCATION: (3)..(27)
<223> OTHER INFORMATION:
<220> FEATURE:
<221> NAME/KEY: mat_peptide
<222> LOCATION: (28)..()
<223> OTHER INFORMATION:

<400> SEQUENCE: 1

Met Gly Val His Glu Cys Pro Ala Trp Leu Trp Leu Leu Leu Ser Leu
    -25                 -20                 -15

Leu Ser Leu Pro Leu Gly Leu Pro Val Leu Gly Ala Pro Pro Arg Leu
    -10                  -5                  -1   1               5

Ile Cys Asp Ser Arg Val Leu Glu Arg Tyr Leu Leu Glu Ala Lys Glu
                 10                  15                  20

Ala Glu Asn Ile Thr Thr Gly Cys Ala Glu His Cys Ser Leu Asn Glu
             25                  30                  35

Asn Ile Thr Val Pro Asp Thr Lys Val Asn Phe Tyr Ala Trp Lys Arg
         40                  45                  50

Met Glu Val Gly Gln Gln Ala Val Glu Val Trp Gln Gly Leu Ala Leu
     55                  60                  65

Leu Ser Glu Ala Val Leu Arg Gly Gln Ala Leu Leu Val Asn Ser Ser
 70                  75                  80                  85

Gln Pro Trp Glu Pro Leu Gln Leu His Val Asp Lys Ala Val Ser Gly
                 90                  95                 100

Leu Arg Ser Leu Thr Thr Leu Leu Arg Ala Leu Gly Ala Gln Lys Glu
                105                 110                 115
```

```
Ala Ile Ser Pro Pro Asp Ala Ala Ser Ala Ala Pro Leu Arg Thr Ile
        120                 125                 130
Thr Ala Asp Thr Phe Arg Lys Leu Phe Arg Val Tyr Ser Asn Phe Leu
135                 140                 145
Arg Gly Lys Leu Lys Leu Tyr Thr Gly Glu Ala Cys Arg Thr Gly Asp
150                 155                 160                 165
Arg

<210> SEQ ID NO 2
<211> LENGTH: 29
<212> TYPE: DNA
<213> ORGANISM: Homo sapiens

<400> SEQUENCE: 2
atctagaagt tgctctctgg acagttcct                                          29

<210> SEQ ID NO 3
<211> LENGTH: 32
<212> TYPE: DNA
<213> ORGANISM: Homo sapiens

<400> SEQUENCE: 3
gaagcttgcg ccaccatggg ggtgcacgaa tg                                      32

<210> SEQ ID NO 4
<211> LENGTH: 27
<212> TYPE: DNA
<213> ORGANISM: Homo sapiens

<400> SEQUENCE: 4
gatcctctag agttgctctc tggacag                                            27

<210> SEQ ID NO 5
<211> LENGTH: 25
<212> TYPE: DNA
<213> ORGANISM: Homo sapiens

<400> SEQUENCE: 5
caacaagctt gcgccgccat ggggg                                              25

<210> SEQ ID NO 6
<211> LENGTH: 4
<212> TYPE: PRT
<213> ORGANISM: Artificial Sequence
<220> FEATURE:
<223> OTHER INFORMATION: Synthetic

<400> SEQUENCE: 6

Ala Ala Ala Ala
1

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Ala Ala Ala Ala Ala
1               5

<210> SEQ ID NO 8
```

```
<211> LENGTH: 5
<212> TYPE: PRT
<213> ORGANISM: Artificial Sequence
<220> FEATURE:
<223> OTHER INFORMATION: Synthetic

<400> SEQUENCE: 8

Gly Gly Gly Gly Gly
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic

<400> SEQUENCE: 9

Gly Gly Gly Gly Gly Gly Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic

<400> SEQUENCE: 10

Gly Gly Pro Gly Gly
1               5

<210> SEQ ID NO 11
<211> LENGTH: 32
<212> TYPE: DNA
<213> ORGANISM: Artificial Sequence
<220> FEATURE:
<223> OTHER INFORMATION: Synthetic oglionucleotide

<400> SEQUENCE: 11
aggtggacag tcgacattat ctgtcccctg tc                                    32

<210> SEQ ID NO 12
<211> LENGTH: 28
<212> TYPE: DNA
<213> ORGANISM: Artificial Sequence
<220> FEATURE:
<223> OTHER INFORMATION: Synthetic oglionucleotide

<400> SEQUENCE: 12
aacaagcttc tagaccacca tgggggtg                                         28

<210> SEQ ID NO 13
<211> LENGTH: 30
<212> TYPE: DNA
<213> ORGANISM: Artificial Sequence
<220> FEATURE:
<223> OTHER INFORMATION: Synthetic oglionucleotide

<400> SEQUENCE: 13
acgacgggct gtaatgaaac gtgcagcttg                                       30

<210> SEQ ID NO 14
<211> LENGTH: 31
<212> TYPE: DNA
<213> ORGANISM: Artificial Sequence
<220> FEATURE:
<223> OTHER INFORMATION: Synthetic oglionucleotide
```

```
<400> SEQUENCE: 14
caagctgcac gtttcattac agcccgtcgt g                              31

<210> SEQ ID NO 15
<211> LENGTH: 39
<212> TYPE: DNA
<213> ORGANISM: Artificial Sequence
<220> FEATURE:
<223> OTHER INFORMATION: Synthetic oglionucleotide

<400> SEQUENCE: 15
gcctggaaga ggatgaatgt cacgcagcag gccgtagaa                      39

<210> SEQ ID NO 16
<211> LENGTH: 40
<212> TYPE: DNA
<213> ORGANISM: Artificial Sequence
<220> FEATURE:
<223> OTHER INFORMATION: Synthetic oglionucleotide

<400> SEQUENCE: 16
ttctacggcc tgctgcgtga cattcatcct cttccaggca                     40

<210> SEQ ID NO 17
<211> LENGTH: 30
<212> TYPE: DNA
<213> ORGANISM: Artificial Sequence
<220> FEATURE:
<223> OTHER INFORMATION: Synthetic oglionucleotide

<400> SEQUENCE: 17
tcttcccagg tgaatgagac cctgcagctg                                30

<210> SEQ ID NO 18
<211> LENGTH: 34
<212> TYPE: DNA
<213> ORGANISM: Artificial Sequence
<220> FEATURE:
<223> OTHER INFORMATION: Synthetic oglionucleotide

<400> SEQUENCE: 18
cagctgcagg gtctcattca cctgggaaga gttg                           34

<210> SEQ ID NO 19
<211> LENGTH: 24
<212> TYPE: DNA
<213> ORGANISM: Artificial Sequence
<220> FEATURE:
<223> OTHER INFORMATION: Synthetic oglionucleotide

<400> SEQUENCE: 19
ccagatccga ccacagctgc tcca                                      24

<210> SEQ ID NO 20
<211> LENGTH: 25
<212> TYPE: DNA
<213> ORGANISM: Artificial Sequence
<220> FEATURE:
<223> OTHER INFORMATION: Synthetic oglionucleotide

<400> SEQUENCE: 20
tggagcagct gtggtcggat ctgga                                     25

<210> SEQ ID NO 21
<211> LENGTH: 28
```

-continued

```
<212> TYPE: DNA
<213> ORGANISM: Artificial Sequence
<220> FEATURE:
<223> OTHER INFORMATION: Synthetic oglionucleotide

<400> SEQUENCE: 21
aacaagcttc tagaccacca tgggggtg                                           28

<210> SEQ ID NO 22
<211> LENGTH: 49
<212> TYPE: DNA
<213> ORGANISM: Artificial Sequence
<220> FEATURE:
<223> OTHER INFORMATION: Synthetic oglionucleotide

<400> SEQUENCE: 22
aggtggacat gtgtgagttt tgtctctgtc ccctctcctg caggcctcc                    49

<210> SEQ ID NO 23
<211> LENGTH: 48
<212> TYPE: DNA
<213> ORGANISM: Artificial Sequence
<220> FEATURE:
<223> OTHER INFORMATION: Synthetic oglionucleotide

<400> SEQUENCE: 23
gaggcctgca ggacagggga cagagacaaa actcacacat gtccacct                     48

<210> SEQ ID NO 24
<211> LENGTH: 47
<212> TYPE: DNA
<213> ORGANISM: Artificial Sequence
<220> FEATURE:
<223> OTHER INFORMATION: Synthetic oglionucleotide

<400> SEQUENCE: 24
tggacagtcg acattattta cccggagaca gggagaggct cttctgc                      47

<210> SEQ ID NO 25
<211> LENGTH: 232
<212> TYPE: PRT
<213> ORGANISM: Homo sapiens

<400> SEQUENCE: 25

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140
```

```
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 26
<211> LENGTH: 1286
<212> TYPE: DNA
<213> ORGANISM: Homo sapiens
<220> FEATURE:
<221> NAME/KEY: CDS
<222> LOCATION: (17)..(1276)
<223> OTHER INFORMATION:

<400> SEQUENCE: 26
aagcttctag accacc atg ggg gtg cac gaa tgt cct gcc tgg ctg tgg ctt      52
               Met Gly Val His Glu Cys Pro Ala Trp Leu Trp Leu
                 1               5                  10 ctc ctg tcc ctg ctg tcg ctc cct ctg ggc ctc cca gtc ctg ggc gcc     100
Leu Leu Ser Leu Leu Ser Leu Pro Leu Gly Leu Pro Val Leu Gly Ala
            15                  20                  25 cca cca cgc ctc atc tgt gac agc cga gtc ctg gag agg tac ctc ttg     148
Pro Pro Arg Leu Ile Cys Asp Ser Arg Val Leu Glu Arg Tyr Leu Leu
        30                  35                  40 gag gcc aag gag gcc gag aat atc acg acg ggc tgt aat gaa acg tgc     196
Glu Ala Lys Glu Ala Glu Asn Ile Thr Thr Gly Cys Asn Glu Thr Cys
45                  50                  55                  60 agc ttg aat gag aat atc act gtc cca gac acc aaa gtt aat ttc tat     244
Ser Leu Asn Glu Asn Ile Thr Val Pro Asp Thr Lys Val Asn Phe Tyr
                65                  70                  75 gcc tgg aag agg atg gag gtc ggg cag cag gcc gta gaa gtc tgg cag     292
Ala Trp Lys Arg Met Glu Val Gly Gln Gln Ala Val Glu Val Trp Gln
            80                  85                  90 ggc ctg gcc ctg ctg tcg gaa gct gtc ctg cgg ggc cag gcc ctg ttg     340
Gly Leu Ala Leu Leu Ser Glu Ala Val Leu Arg Gly Gln Ala Leu Leu
        95                  100                 105 gtc aac tct tcc cag gtg aat gag acc ctg cag ctg cat gtg gat aaa     388
Val Asn Ser Ser Gln Val Asn Glu Thr Leu Gln Leu His Val Asp Lys
    110                 115                 120 gcc gtc agt ggc ctt cgc agc ctc acc act ctg ctt cgg gct ctg gga     436
Ala Val Ser Gly Leu Arg Ser Leu Thr Thr Leu Leu Arg Ala Leu Gly
125                 130                 135                 140 gcc cag aag gaa gcc atc tcc cct cca gat gcg gcc tca gct gct cca     484
Ala Gln Lys Glu Ala Ile Ser Pro Pro Asp Ala Ala Ser Ala Ala Pro
                145                 150                 155 ctc cga aca atc act gct gac act ttc cgc aaa ctc ttc cga gtc tac     532
Leu Arg Thr Ile Thr Ala Asp Thr Phe Arg Lys Leu Phe Arg Val Tyr
            160                 165                 170 tcc aat ttc ctc cgg gga aag ctg aag ctg tac aca ggg gag gcc tgc     580
Ser Asn Phe Leu Arg Gly Lys Leu Lys Leu Tyr Thr Gly Glu Ala Cys
        175                 180                 185
```

```
agg aca ggg gac aga gac aaa act cac aca tgt cca cct tgt cca gct      628
Arg Thr Gly Asp Arg Asp Lys Thr His Thr Cys Pro Pro Cys Pro Ala
    190                 195                 200 ccg gaa ctc ctg ggg ggt cct tca gtc ttc ctc ttc ccc cca aaa ccc      676
Pro Glu Leu Leu Gly Gly Pro Ser Val Phe Leu Phe Pro Pro Lys Pro
205                 210                 215                 220 aag gac acc ctc atg atc tcc cgg acc cct gag gtc aca tgc gtg gtg      724
Lys Asp Thr Leu Met Ile Ser Arg Thr Pro Glu Val Thr Cys Val Val
                225                 230                 235 gtg gac gtg agc cac gaa gac cct gag gtc aag ttc aac tgg tac gtg      772
Val Asp Val Ser His Glu Asp Pro Glu Val Lys Phe Asn Trp Tyr Val
        240                 245                 250 gac ggc gtg gag gtg cat aat gcc aag aca aag ccg cgg gag gag cag      820
Asp Gly Val Glu Val His Asn Ala Lys Thr Lys Pro Arg Glu Glu Gln
                255                 260                 265 tac aac agc acg tac cgt gtg gtc agc gtc ctc acc gtc ctg cac cag      868
Tyr Asn Ser Thr Tyr Arg Val Val Ser Val Leu Thr Val Leu His Gln
    270                 275                 280 gac tgg ctg aat ggc aag gag tac aag tgc aag gtc tcc aac aaa gcc      916
Asp Trp Leu Asn Gly Lys Glu Tyr Lys Cys Lys Val Ser Asn Lys Ala
285                 290                 295                 300 ctc cca gcc ccc atc gag aaa acc atc tcc aaa gcc aaa ggg cag ccc      964
Leu Pro Ala Pro Ile Glu Lys Thr Ile Ser Lys Ala Lys Gly Gln Pro
                305                 310                 315 cga gaa cca cag gtg tac acc ctg ccc cca tcc cgg gat gag ctg acc     1012
Arg Glu Pro Gln Val Tyr Thr Leu Pro Pro Ser Arg Asp Glu Leu Thr
        320                 325                 330 aag aac cag gtc agc ctg acc tgc ctg gtc aaa ggc ttc tat ccc agc     1060
Lys Asn Gln Val Ser Leu Thr Cys Leu Val Lys Gly Phe Tyr Pro Ser
                335                 340                 345 gac atc gcc gtg gag tgg gag agc aat ggg cag ccg gag aac aac tac     1108
Asp Ile Ala Val Glu Trp Glu Ser Asn Gly Gln Pro Glu Asn Asn Tyr
    350                 355                 360 aag acc acg cct ccc gtg ctg gac tcc gac ggc tcc ttc ttc ctc tac     1156
Lys Thr Thr Pro Pro Val Leu Asp Ser Asp Gly Ser Phe Phe Leu Tyr
365                 370                 375                 380 agc aag ctc acc gtg gac aag agc agg tgg cag cag ggg aac gtc ttc     1204
Ser Lys Leu Thr Val Asp Lys Ser Arg Trp Gln Gln Gly Asn Val Phe
                385                 390                 395 tca tgc tcc gtg atg cat gag gct ctg cac aac cac tac acg cag aag     1252
Ser Cys Ser Val Met His Glu Ala Leu His Asn His Tyr Thr Gln Lys
        400                 405                 410 agc ctc tcc ctg tct ccg ggt aaa taatgtcgac                          1286
Ser Leu Ser Leu Ser Pro Gly Lys
                415                 420

<210> SEQ ID NO 27
<211> LENGTH: 420
<212> TYPE: PRT
<213> ORGANISM: Homo sapiens

<400> SEQUENCE: 27

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Asn Glu Thr Cys Ser Leu Asn Glu
    50                  55                  60
```

```
Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
            100                 105                 110

Gln Val Asn Glu Thr Leu Gln Leu His Val Asp Lys Ala Val Ser Gly
            115                 120                 125

Leu Arg Ser Leu Thr Thr Leu Leu Arg Ala Leu Gly Ala Gln Lys Glu
            130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg Asp Lys Thr His Thr Cys Pro Pro Cys Pro Ala Pro Glu Leu Leu
            195                 200                 205

Gly Gly Pro Ser Val Phe Leu Phe Pro Pro Lys Pro Lys Asp Thr Leu
            210                 215                 220

Met Ile Ser Arg Thr Pro Glu Val Thr Cys Val Val Val Asp Val Ser
225                 230                 235                 240

His Glu Asp Pro Glu Val Lys Phe Asn Trp Tyr Val Asp Gly Val Glu
                245                 250                 255

Val His Asn Ala Lys Thr Lys Pro Arg Glu Glu Gln Tyr Asn Ser Thr
            260                 265                 270

Tyr Arg Val Val Ser Val Leu Thr Val Leu His Gln Asp Trp Leu Asn
            275                 280                 285

Gly Lys Glu Tyr Lys Cys Lys Val Ser Asn Lys Ala Leu Pro Ala Pro
            290                 295                 300

Ile Glu Lys Thr Ile Ser Lys Ala Lys Gly Gln Pro Arg Glu Pro Gln
305                 310                 315                 320

Val Tyr Thr Leu Pro Pro Ser Arg Asp Glu Leu Thr Lys Asn Gln Val
                325                 330                 335

Ser Leu Thr Cys Leu Val Lys Gly Phe Tyr Pro Ser Asp Ile Ala Val
            340                 345                 350

Glu Trp Glu Ser Asn Gly Gln Pro Glu Asn Asn Tyr Lys Thr Thr Pro
            355                 360                 365

Pro Val Leu Asp Ser Asp Gly Ser Phe Phe Leu Tyr Ser Lys Leu Thr
            370                 375                 380

Val Asp Lys Ser Arg Trp Gln Gln Gly Asn Val Phe Ser Cys Ser Val
385                 390                 395                 400

Met His Glu Ala Leu His Asn His Tyr Thr Gln Lys Ser Leu Ser Leu
                405                 410                 415

Ser Pro Gly Lys
            420
```